(12) United States Patent
Suetoshi et al.

(10) Patent No.: US 8,256,295 B2
(45) Date of Patent: Sep. 4, 2012

(54) METHOD AND APPARATUS FOR MEASURING SPEED-OF-SOUND

(75) Inventors: Ryoichi Suetoshi, Nishinomiya (JP);
Dorian Cretin, Nishinomiya (JP);
Atsushi Uodome, Nishinomiya (JP)

(73) Assignee: Furuno Electric Company, Ltd., Nishinomiya, Hyogo-Pref. (JP)

( * ) Notice: Subject to any disclaimer, the term of this patent is extended or adjusted under 35 U.S.C. 154(b) by 309 days.

(21) Appl. No.: 12/759,486

(22) Filed: Apr. 13, 2010

(65) Prior Publication Data

US 2010/0257935 A1 Oct. 14, 2010

(30) Foreign Application Priority Data

Apr. 14, 2009 (JP) ................................. 2009-098414

(51) Int. Cl.
*G01N 29/07* (2006.01)
(52) U.S. Cl. ........................................... 73/597; 73/602
(58) Field of Classification Search .................... 73/597, 73/602, 626, 628
See application file for complete search history.

(56) References Cited

U.S. PATENT DOCUMENTS

| 5,426,979 | A | | 6/1995 | Kantorovich et al. | |
|---|---|---|---|---|---|
| 5,817,018 | A | * | 10/1998 | Ohtomo | 600/437 |
| 5,902,240 | A | | 5/1999 | Ishii et al. | |
| 7,002,876 | B2 | * | 2/2006 | Komai et al. | 367/99 |
| 7,694,565 | B2 | * | 4/2010 | Koerdt et al. | 73/597 |
| 7,753,848 | B2 | * | 7/2010 | Haimerl | 600/443 |
| 7,942,819 | B2 | * | 5/2011 | Arai | 600/437 |

FOREIGN PATENT DOCUMENTS

| EP | 2153778 A1 | 2/2010 |
|---|---|---|
| JP | 2003-517328 A | 5/2003 |
| WO | WO 97/13145 A1 | 4/1997 |
| WO | WO 99/45348 A1 | 9/1999 |
| WO | WO 03/099132 A1 | 12/2003 |

* cited by examiner

*Primary Examiner* — J M Saint Surin
(74) *Attorney, Agent, or Firm* — Birch, Stewart, Kolasch & Birch, LLP

(57) ABSTRACT

A speed-of-sound measurement apparatus includes a wave transmission module for transmitting an ultrasonic wave to a front surface of a subject's body, a plurality of wave reception modules which each receives the ultrasonic wave from the subject's body and outputs a waveform signal corresponding to the received ultrasonic wave, a presumed propagation time calculating module for calculating a propagation time from when the ultrasonic wave is transmitted by the wave transmission module to when the ultrasonic wave arrives at each of the wave reception modules after propagating along the front surface of the subject's body or inside the subject's body, based on a presumed value of speed-of-sound in the subject's body and a front surface shape of the subject's body, a validity index value calculating module for finding a validity index value to be an index of validity of the propagation time based on the waveform signals outputted by at least two of the plurality of wave reception modules, and a speed-of-sound deriving module for finding the speed-of-sound in the subject's body based on the validity index value.

14 Claims, 17 Drawing Sheets

METHOD AND APPARATUS FOR MEASURING SPEED-OF-SOUND

CROSS-REFERENCE TO RELATED APPLICATION(S)

This application claims priority under 35 U.S.C. §119 to Japanese Patent Application No. 2009-098414, which was filed on Apr. 14, 2009, the entire disclosure of which is hereby incorporated by reference.

TECHNICAL FIELD

The present invention relates to an apparatus and a method for measuring speed-of-sound. Specifically, the invention relates to a technique for enabling an accurate and stable measurement in the apparatus and method for measuring speed-of-sound in a subject's body to be measured from the outside of the body using an ultrasonic wave.

BACKGROUND

JP2003-517328(A) discloses an ultrasonic diagnostic apparatus for evaluating a bone using ultrasonic waves. The ultrasonic diagnostic apparatus emits an ultrasonic pulse and receives an ultrasonic wave which is propagated in a cortical bone and emitted from the cortical bone. Then, the ultrasonic diagnostic apparatus measures a period of period of time from the time of transmitting the ultrasonic wave to the time of receiving the same, and finds speed-of-sound in the cortical bone from a propagation path known.

Since the speed-of-sound in an object varies depending on the elastic property of the object, measurement of speed-of-sound in the bone can be used for an index of bone strength (health of the bone). The ultrasonic diagnostic apparatus of JP2003-517328(A) uses the speed-of-sound obtained as above as an evaluation value of the bone.

In a case of a configuration where a time interval from the time of transmitting the ultrasonic pulse wave to the time of receiving the same is measured by a timer like in the case of JP2003-517328(A), a peak of the pulse of the received wave must be adequately detected from among waveform signals outputted by a transducer. Here, in a case of an ideal condition (for example, measurement of an object located in water), it is relatively easy to detect the pulse of the received wave. However, in an actual measurement using a living body as a subject, since fat and water are mixed in the propagation path of the ultrasonic wave, various noises are generated, for example, an unnecessary echo is generated, an unnecessary waveform is superimposed due to the reflection from a back surface of the cortical bone and the like.

As for this point, in the configuration of JP2003-517328 (A), if the noises are contained in the waveform signal from among the waveform signals, it becomes difficult to detect the necessary pulse of the received wave, and it has not been possible to stably measure the period of time from the time of transmitting the ultrasonic pulse wave to the time of receiving the same ultrasonic pulse. Therefore, if an examination of the bone strength is tried on the actual site, an accurate result is difficult to obtain and there remains room for improvement.

SUMMARY

The present application invention has been made in consideration of the above circumstances, and provides an apparatus and a method for measuring speed-of-sound which can accurately and stably find the speed-of-sound.

According to a first aspect of the invention, a speed-of-sound measurement apparatus having a configuration as below is provided. That is, the speed-of-sound measurement apparatus includes a wave transmission module, a plurality of wave reception modules, a presumed propagation time calculating module, a validity index value calculating module, and a speed-of-sound deriving module. The wave transmission module transmits an ultrasonic wave to a front surface of a subject's body. The wave reception modules each receive the ultrasonic wave from the subject's body, and output a waveform signal in response to the received ultrasonic wave. The presumed propagation time calculating module calculates a propagation time from when the ultrasonic wave is transmitted by the wave transmission module to when the ultrasonic wave arrives at each of the wave reception modules after propagating along the front surface of the subject's body or inside the subject's body based on a presumed value of speed-of-sound in the subject's body and the shape of the front surface of the subject's body. The validity index value calculating module finds a validity index value to be an index of validity of the propagation time based on the waveform signals outputted by at least two of the plurality of wave reception modules. The speed-of-sound deriving module finds the speed-of-sound in the subject's body based on the validity index value.

That is, by determining the validity of the propagation time, determination can be performed of whether or not the speed-of-sound value presumed in calculating the propagation time is correct. This makes it possible to find the speed-of-sound in the subject's body. Here, it is not strictly necessary to detect the position of the peak of the received waveform when determining the validity of the propagation time. Therefore, even if the received waveform includes a noise, the speed-of-sound can be adequately found. Further, the validity of the propagation time is determined based on the waveform signals from the plurality of wave reception modules allowing the effect of the noise to be reduced.

In the speed-of-sound measurement apparatus, the validity index value calculating module may preferably shift respectively to the waveform signals outputted by at least two of the plurality of wave reception modules by the time corresponding to the propagation time, find a integrated waveform obtained by integrating the shifted waveform signals to each other, and find the validity index value based on the integrated waveform.

Specifically, when the waveform signals outputted by the wave reception modules are integrated to each other, in the case where the peak positions of the waveforms coincide, the amplitudes are most strengthened with each other. By using the aforementioned property, only a desired peak can be emphasized to lower the effects of other noises. With the above configuration, if the speed-of-sound presumed by the presumed propagation time calculating module is correct, the peak positions of the integrated waveform signals coincide to strengthen the amplitudes with each other. Therefore, even if the waveform signal outputted by the wave reception module includes a noise, determination can be performed of whether or not the presumed value of speed-of-sound is correct by observing the integrated waveform.

In the speed-of-sound measurement apparatus, the validity index value calculating module may shift the waveform signals outputted by at least two of the plurality of wave reception modules by a time corresponding to the propagation time, find a multiplied waveform obtained by multiplying the shifted waveform signals by each other, and find the validity index value based on the multiplied waveform.

Specifically, when the waveform signals outputted by the wave reception modules are multiplied by each other, in the case where the peak positions of the waveforms coincide, the amplitudes are most strengthened with each other. By using the aforementioned property, only a desired peak can be emphasized to lower the effects of other noises. With the above configuration, if the speed-of-sound presumed by the presumed propagation time calculating module is correct, the peak positions of the multiplied waveform signals coincide to strengthen the amplitudes with each other. Therefore, even if the waveform signal outputted by the wave reception module includes a noise, determination can be performed of whether or not the presumed value of speed-of-sound is correct by observing the multiplied waveform.

The speed-of-sound measurement apparatus may preferably be configured as follows. That is, the presumed propagation time calculating module may calculate the propagation time using plural kinds of values as the presumed value of speed-of-sound. The validity index value calculating module may find, in response to the plural kinds of presumed values of speed-of-sound, the validity index value for each kind. The speed-of-sound deriving module may find the speed-of-sound in the subject's body based on the validity index value for each of the plural kinds of presumed values of speed-of-sound.

This makes it possible for the case in which the propagation time obtained by testing the plural kinds of presumed values of speed-of-sound is most valid and the presumed value of speed-of-sound when calculating the propagation time is employed as the measurement value of the speed-of-sound in the subject's body.

In the speed-of-sound measurement apparatus, the presumed propagation time calculating module may preferably calculate the propagation time based on the shape of the front surface of the subject's body measured in advance.

This makes it possible to calculate the presumed propagation time with the actual shape of the front surface of the subject's body taken into consideration; therefore, speed-of-sound can be accurately found even if the shape of the front surface of the subject's body is curved, for example.

The speed-of-sound measurement apparatus may preferably be configured as follows. That is, the speed-of-sound measurement apparatus may include a shape detecting module. At least a part of the plurality of wave reception modules may be configured to transmit the ultrasonic wave to the front surface of the subject's body. The shape detecting module may detect the shape of the front surface of the subject's body based on the period of time from when the ultrasonic wave is transmitted to when the ultrasonic wave arrives at each of the wave reception modules after reflected on the front surface of the subject's body. The presumed propagation time calculating module may calculate the propagation time based on the shape of the front surface of the subject's body detected by the shape detecting module.

This makes it possible to detect the shape of the front surface of the subject's body using a part of the configuration for measuring the speed-of-sound, enabling the apparatus to be simplified to reduce the cost.

The speed-of-sound measurement apparatus may be configured as follows. That is, the plurality of wave reception modules may constitute a linear array in which the wave reception modules are arranged at an equal interval in one line, and at least any one of the plurality of wave reception modules functions as the wave transmission module.

This enables the transmission dedicated configuration to be eliminated, allowing the apparatus to be simplified. Further, the timing is shifted when the ultrasonic wave is transmitted from each of the adjacent plurality of wave reception modules and the time interval for shifting the timing is adjusted so that the ultrasonic wave beam can be created at any angle. This enables the ultrasonic wave to be radiated to the front surface of the subject's body at an optimal angle. Moreover, in the case of the configuration where the front surface shape of the subject's body is detected based on the period of time from when the ultrasonic wave is transmitted to the subject's body from the wave reception module to when the reflected wave arrives at each wave reception module, only the front surface shape at the position immediately below the wave reception module can be detected. Therefore, in the case of the configuration where the wave transmission module and the wave reception module are arranged separately, the front surface shape of a portion immediately below the wave transmission module cannot be detected. In this regard, since the wave reception module functions as the wave transmission module, the front surface shape of the portion immediately below the wave reception module as the wave transmission module can be detected. This makes it possible to correctly calculate the propagation time.

According to a second aspect of the invention, provided as follows is a method for measuring speed-of-sound in a subject's body using a speed-of-sound measurement apparatus including a plurality of wave reception modules where each outputs a waveform signal in response to an ultrasonic wave received. That is, the method includes a wave transmitting step, a wave receiving step, a presumed propagation time calculating step and a validity index value calculating step. The wave transmitting step transmits an ultrasonic wave to a front surface of the subject's body. The wave receiving step receives the ultrasonic wave from the subject's body by each of the plurality of wave reception modules. The presumed propagation time calculating step calculates a propagation time from when the ultrasonic wave is transmitted in the wave transmitting step to when the ultrasonic wave arrives at each of the wave reception modules after propagating along the front surface of the subject's body or inside the subject's body, based on a presumed value of speed-of-sound in the subject's body and the front surface shape of the subject's body. The validity index value calculating step finds a validity index value to be an index of validity of the propagation time based on the waveform signals outputted by at least two of the plurality of wave reception modules. The presumed propagation time calculating step and the validity index value calculating step are repeated with the presumed value of speed-of-sound being varied so the validity index value is found for each of the plural kinds of presumed values of speed-of-sound and the speed-of-sound in the subject's body is found based on the validity index value for the each kind.

That is, by determining the validity of the propagation time, determination can be made of whether or not the speed-of-sound value presumed in calculating the relevant propagation time is correct. This makes it possible to find the speed-of-sound in the subject's body. Here, it is not strictly necessary to detect the position of the peak of the received waveform when determining the validity of the propagation time. Therefore, even if the received waveform includes a noise, the speed-of-sound can be adequately found. Further, the validity of the propagation time is determined based on the waveform signals from the plurality of wave reception modules, allowing the effect of the noise to be reduced. Then, in the case where the propagation time obtained by testing the plural kinds of presumed values of speed-of-sound is most valid, the presumed value of speed-of-sound when calculating the relevant propagation time can be employed as the measurement value of the speed-of-sound in the subject's body.

The speed-of-sound measurement method may preferably employ the following steps. That is, in the validity index value calculating step, the waveform signals outputted by at least two the plurality of wave reception modules may be shifted respectively by a time corresponding to the propagation time, the shifted waveform signals may be integrated to each other to find an integrated waveform, and the validity index value may be found based on the integrated waveform.

Specifically, when the waveform signals outputted by the wave reception modules are integrated to each other, in the case where the peak positions of the waveforms coincide, the amplitudes are most strengthened with each other. By using the aforementioned property, only a desired peak can be emphasized to lower the effects of other noises. With the above configuration, if the speed-of-sound presumed in the presumed propagation time calculating step is correct, the peak positions of the integrated waveform signals coincide to strengthen the amplitudes with each other. Therefore, even if the waveform signal outputted by the wave reception module includes a noise, determination can be performed whether or not the presumed value of speed-of-sound is correct by observing the amplitude of the integrated waveform.

The speed-of-sound measurement method may preferably also employ the following steps. That is, in the validity index value calculating step, the waveform signals outputted by at least two the plurality of wave reception modules may be shifted respectively by a time corresponding to the propagation time, the shifted waveform signals may be multiplied by each other to find a multiplied waveform, and the validity index value may be found based on the multiplied waveform.

Specifically, when the waveform signals outputted by the wave reception modules are multiplied by each other, in the case where the peak positions of the waveforms coincide, the amplitudes are most strengthened with each other. By using the aforementioned property, only a desired peak can be emphasized to lower the effects of other noises. With the above configuration, if the speed-of-sound presumed in the presumed propagation time calculating step is correct, the peak positions of the multiplied waveform signals coincide to strengthen the amplitudes with each other. Therefore, even if the waveform signal outputted by the wave reception module includes a noise, determination can be performed whether or not the presumed value of speed-of-sound is correct by observing the amplitude of the multiplied waveform.

The speed-of-sound measurement method may preferably employ the following steps. That is, the method may include a shape detecting step detecting the front surface shape of the subject's body. The propagation time may be calculated based on the front surface shape in the presumed propagation time calculating step.

This makes it possible to calculate the presumed propagation time with the actual front surface shape of the subject's body taken into consideration; therefore, the speed-of-sound can be accurately found even if the front surface shape of the subject's body is curved, for example.

BRIEF DESCRIPTION OF THE DRAWINGS

The present disclosure is illustrated by way of example and not by way of limitation in the figures of the accompanying drawings in which the like reference numerals indicate like elements and in which.

DETAILED DESCRIPTION

Figure 1:
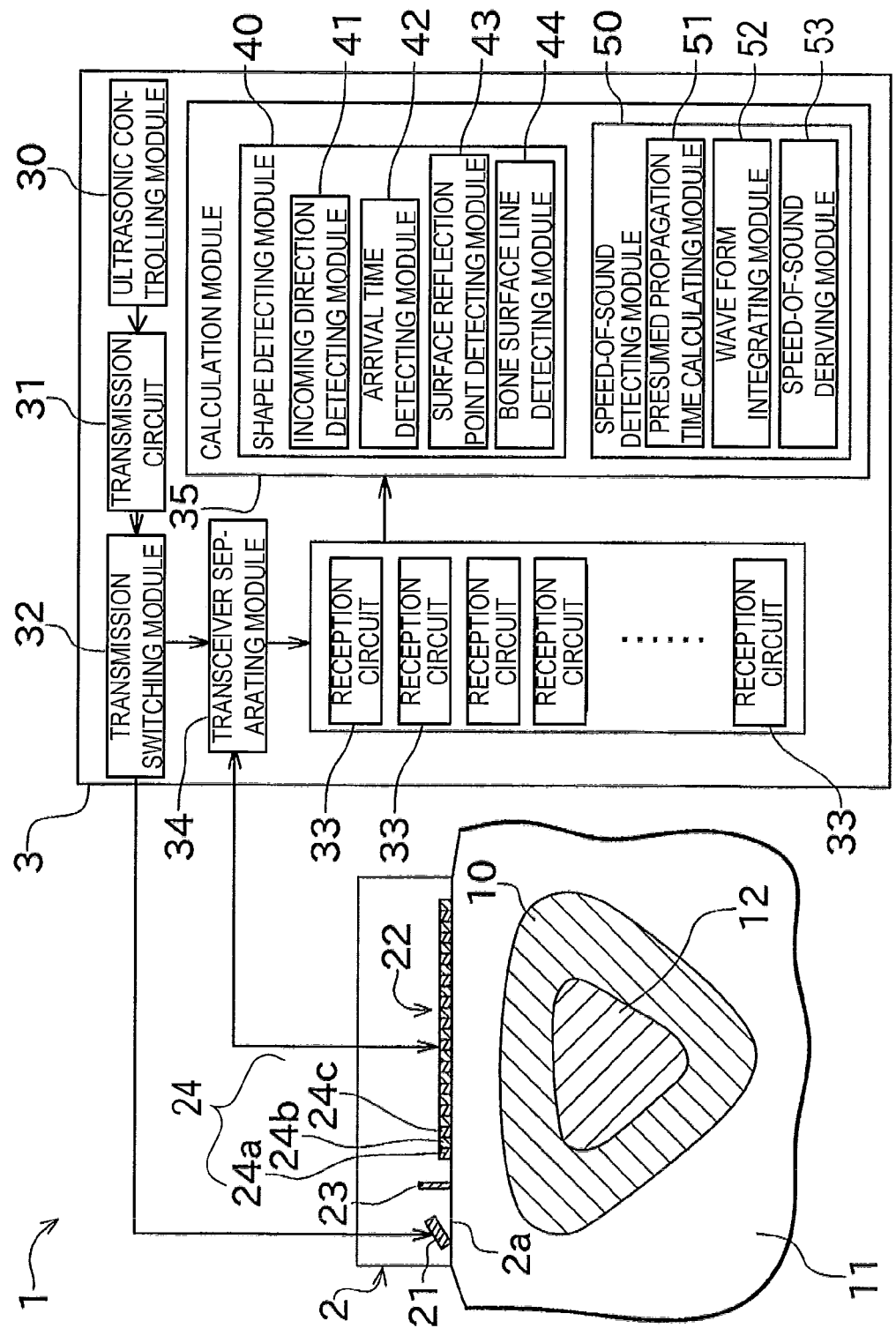
FIG. 1 shows a schematic cross-sectional view of a bone strength diagnostic apparatus and a functional block diagram thereof according to an embodiment of the invention.

Next, an embodiment of the invention will be described with reference to the appended drawings. FIG. 1 shows a schematic cross-sectional view and a functional block diagram of a bone strength diagnostic apparatus 1 as a speed-of-sound measurement apparatus according to this embodiment.

The bone strength diagnostic apparatus 1 is used for examining bone strength of a cortical bone of, for example, long bones such as the tibia (but, not limited thereto). Specifically, a bone is generally made up of a cortical bone 10 and a tracery-shape cancellous spongy bone 12 located inside the cortical bone 10. Further, the cortical bone 10 is covered by a soft tissue 11 such as muscle and fat. The bone strength diagnostic apparatus 1 of this embodiment is configured to emit an ultrasonic wave from outside the soft tissue 11 to the cortical bone 10 to measure speed-of-sound (bone speed-of-sound) in the cortical bone 10.

FIG. 1 shows on the left side thereof a cross-sectional view of a human shank cut along a plane perpendicular to a longitudinal direction of a bone of the shank. As shown in FIG. 1, a front surface (upper side in this figure) of the cortical bone 10 has a gently curved contour radially bulging (in a direction perpendicular to the longitudinal direction of the bone). Consequently, in the following description, there may be a case where the long bone is treated as a cylinder, and a direction in the cross-section thereof in which the ultrasonic wave propagates along the front surface of the cortical bone 10 is referred to as a circumferential direction. On the other hand, although not shown, in a section cut along a plane parallel to the longitudinal direction of the bone, the cortical bone 10 has a substantially linear surface contour.

However, since the human bone has aeolotropy, the speed-of-sound in the longitudinal direction and the speed-of-sound in the circumferential direction are different with each other. Therefore, it is important to measure the speed-of-sounds of the circumferential direction and longitudinal direction to investigate anisotropic structures thereof when examining the bone strength. Thus, the bone strength diagnostic apparatus 1 of this embodiment is configured so that even if, as in a case of measuring the speed-of-sound of the bone in the circumferential direction, a measurement target has a cross-section contour curved, the speed-of-sound can be accurately measured.

Hereinafter, the configuration of the bone strength diagnostic apparatus 1 is specifically described. As shown in FIG. 1, the bone strength diagnostic apparatus 1 includes an ultrasonic transceiver 2 and an apparatus main body 3.

The ultrasonic transceiver 2 transmits and receives the ultrasonic wave. This ultrasonic transceiver 2 includes a contact face 2a contacting with a surface of the soft tissue 11 of a measurement site, an ultrasonic transmission dedicated transducer 21, an array transducer 22, and a sound insulating member 23. The array transducer 22 includes a plurality of transducers 24 arranged in one line. Further, the ultrasonic transmission dedicated transducer 21 and the sound insulating member 23 are aligned in a direction along the direction of the array transducer 22 arrayed. Note that as the transducers used in this embodiment are those in which emit the ultrasonic wave with the surface thereof being vibrated when given an electrical signal, and generate and output an electrical signal when receiving the ultrasonic wave on the surface thereof.

The ultrasonic transmission dedicated transducer 21 (wave transmission module) is located so that a surface thereof is inclined to the contact face 2a, and configured so as to transmit the ultrasonic wave in an oblique direction from the contact face 2a. The ultrasonic transmission dedicated transducer 21 is used, which has a weak directionality of the ultrasonic wave emitted (an angular range of the ultrasonic wave is large).

The array transducer 22 includes the plurality of transducers 24 (wave reception module). Note that in the following description, the plurality of transducers 24, if necessary to be discerned, may be added with a lowercase alphabet at the end of the numeral thereof from the side closer to the ultrasonic transmission dedicated transducer 21, and represented by a transducer 24a, a transducer 24b, a transducer 24c, etc. The transducers 24 are arranged so as to be parallel to the contact face 2a at an equal interval in one line. Moreover, each of the transducers 24 is configured to be able to transmit and receive the ultrasonic wave.

The sound insulating member 23 is formed into a plate, and located between the ultrasonic transmission dedicated transducer 21 and the array transducer 22. The sound insulating member 23 is for preventing the ultrasonic wave transmitted from the ultrasonic transmission dedicated transducer 21 from propagating in the ultrasonic transceiver 2 and directly reach the array transducer 22. Note that as materials of the sound insulating member 23 employed are those having sound absorbability such as cork, synthetic rubber, and porous material (e.g., foamed resin), for example.

In a case where the ultrasonic transceiver 2 is used to actually transmit and receive the ultrasonic wave, a skin surface of the measurement site (that is, an outer surface of the soft tissue 11) is applied with ultrasonic wave jelly, and the skin surface is brought into contact with the contact face 2a. Then, the ultrasonic transmission dedicated transducer 21 or the array transducer 22 transmits the ultrasonic wave. With the aforementioned operation, the ultrasonic wave impinges on the cortical bone 10 as a measurement target through the soft tissue 11. Then, the ultrasonic wave returning from the cortical bone 10 is received by the array transducer 22. Note that the ultrasonic wave jelly prevents a gap from being generated between the soft tissue 11 and the contact face 2a, and an acoustic impedance is matched between the contact face 2a and the soft tissue 11 to suppress the ultrasonic wave which is transmitted from the ultrasonic transmission dedicated transducer 21 or the array transducer 22 from being reflected on the surface of the soft tissue 11.

Next, the apparatus main body 3 is described. The apparatus main body 3 is coupled to the ultrasonic transceiver 2 via cables, and configured to be able to transmit and receive a signal to and from the ultrasonic transceiver 2. Specifically, the apparatus main body 3 includes an ultrasonic controlling module 30, a transmission circuit 31, a transmission switching module 32, a plurality of reception circuits 33, a transceiver separating module 34, and a calculation module 35.

The transmission circuit 31 is configured to generate an electrical pulse signal for vibrating the ultrasonic transmission dedicated transducer 21 or the array transducer 22 to generate the ultrasonic wave, and to send the electrical pulse signal to the transmission switching module 32. A center frequency of an electrical pulse vibration is, for example, from about 1 to 10 MHz. Note that a chirp signal may be used instead of the electrical pulse signal, for example.

Note that the transmission circuit 31 is configured to be able to generate the electrical pulse signal at any timing for each of the plurality of transducers 24 in a case of generating the ultrasonic wave by the array transducer 22. Further, the ultrasonic controlling module 30 is coupled to the transmission circuit 31 and configured to send to the transmission circuit 31a control signal for transmitting the ultrasonic wave from the plurality of transducers 24. With the configuration, the control can be performed so that the ultrasonic wave is transmitted simultaneously or at individual timings from the plurality of transducers 24.

The transmission switching module 32 is configured to switch whether to send the electrical pulse signal sent from the transmission circuit 31 toward the ultrasonic transmission dedicated transducer 21 or the array transducer 22. That is, the transmission switching module 32 selects the transducer to transmit the ultrasonic wave.

The plurality of reception circuits 33 are correspondingly coupled to the plurality of transducers 24 constituting the array transducer 22. Each of the reception circuits 33 is configured to receive the electrical signal which one transducer 24 outputs by receiving the ultrasonic wave, subject the relevant electrical signal to an amplification process, a filtering process, a digital conversion process and the like to generate a digital signal, and send the digital signal to the calculation module 35. Note that the signal directly outputted from the array transducer 22 is an analogue waveform signal, and whereas the signal sent to the calculation module 35 is a digital waveform signal subjected to the signal process, they may not be distinguished from each other and referred to simply as "waveform signal" in the following description.

The transceiver separating module 34 is coupled to the array transducer 22 between the transmission circuit 31 and the reception circuit 33. The transceiver separating module 34 prevents the electrical signal (electrical pulse signal) sent from the transmission circuit 31 to the array transducer 22 from being directly flown to the reception circuit 33, and prevents the electrical signal sent from the array transducer 22 to the reception circuit 33 from being flown to a side of the transmission circuit 31.

Next, description is given of a case where the ultrasonic transmission dedicated transducer 21 transmits the ultrasonic wave. In a case of transmitting the ultrasonic wave by the ultrasonic transmission dedicated transducer 21, the transmission switching module 32 determines the ultrasonic transmission dedicated transducer 21 as a transducer to transmit ultrasonic waves. Then, when the pulse signal from the transmission circuit 31 is sent to the ultrasonic transmission dedicated transducer 21, the ultrasonic transmission dedicated transducer 21 transmits the ultrasonic wave modulated in pulses to the cortical bone 10 in an oblique direction.

The ultrasonic wave transmitted from the ultrasonic transmission dedicated transducer 21 is received by the array transducer 22 via a plurality of propagation paths. When the array transducer 22 receives the ultrasonic wave, the waveform signal is sent from each transducer 24 to the calculation module 35.

Figure 2:
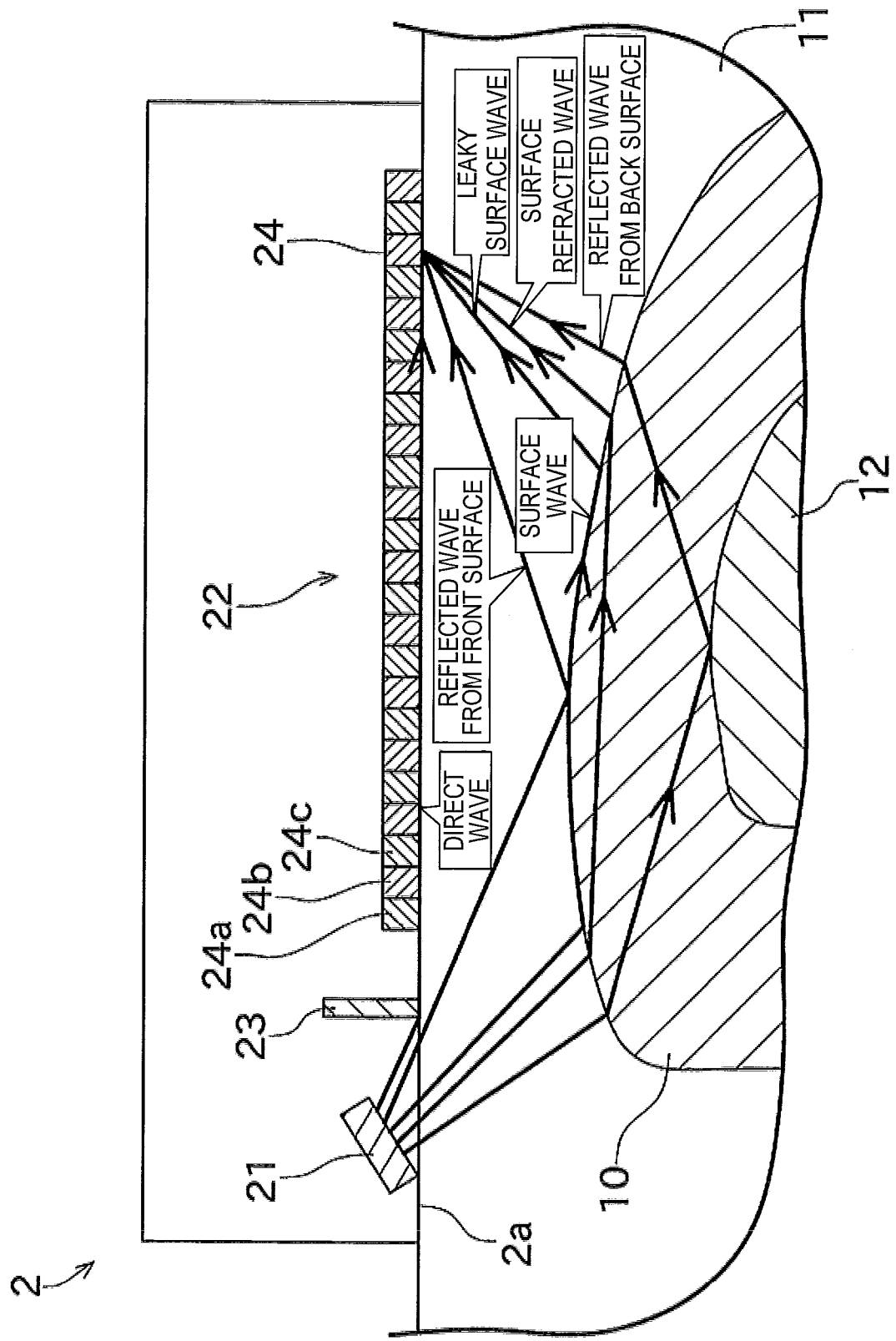
FIG. 2 is a conceptual diagram illustrating a plurality of propagation paths of an ultrasonic wave.

Description is given of the plurality of propagation paths through which propagated is the ultrasonic wave sent from the ultrasonic transmission dedicated transducer 21 with reference to FIG. 2. FIG. 2 is a diagram conceptually showing the plurality of propagation paths of the ultrasonic wave to reach a certain transducer 24. Note that only the ultrasonic wave to reach one transducer 24 is shown in FIG. 2, but actually the ultrasonic wave reaches every transducer 24 via the plurality of paths.

As shown in FIG. 2, a direct wave is an ultrasonic wave which is transmitted from the ultrasonic transmission dedicated transducer 21, is propagated along the surface of the soft tissue 11, and directly reaches the transducer 24. A reflected wave from the front surface is an ultrasonic wave which is transmitted from the ultrasonic transmission dedicated transducer 21, propagated in the soft tissue 11, reflected on the front surface of the cortical bone 10 (boundary plane between the soft tissue 11 and the cortical bone 10), and reaches the transducer 24. Further, a reflected wave from the back surface is an ultrasonic wave which is propagated in the soft tissue 11, enters the cortical bone 10 to be propagated therein, is reflected on the back surface of the cortical bone 10 (boundary plane between the cortical bone 10 and the cancellous spongy bone 12), and thereafter, emitted again in the soft tissue 11 to reach the transducer 24.

Additionally, in some cases, the ultrasonic wave transmitted from the ultrasonic transmission dedicated transducer 21 propagates in the soft tissue 11, impinges on the cortical bone 10, propagates near the front surface of the cortical bone 10, and again is emitted in the soft tissue 11 to reach the transducer 24. In this specification, the ultrasonic wave received via the propagation path like this is referred to as the surface propagation wave. The surface propagation wave includes two propagation paths of a leaky surface wave and surface refracted wave.

When the ultrasonic wave impinges on the front surface of the cortical bone 10 at a critical angle, a surface wave is generated on the front surface of the cortical bone 10. The surface wave emits a leaky wave in a predetermined direction (direction in which an output angle is a critical angle) on the soft tissue 11 side while propagating along the front surface of the cortical bone 10. At this time, the leaky wave received by the transducer 24 is referred to as the leaky surface wave. On the other hand, the ultrasonic wave, when impinging on the front surface of the cortical bone 10 at an angle smaller than the critical angle, is refracted on the front surface of the cortical bone 10. At this time, the ultrasonic wave, when entering at an incident angle close to the critical angle, propagates in the interior but near the front surface of the cortical bone 10, and thereafter, is refracted on the front surface of the cortical bone 10 to the array transducer 22 side to be emitted in the soft tissue 11. The ultrasonic wave received at this time is referred to as the surface refracted wave in this specification. The surface refracted wave is generated only when a section contour shape of the cortical bone 10 is curved.

Note that there may be cases where some of the above plural types of ultrasonic waves are not generated or not received by the transducers 24 even if generated, depending on the conditions such as the shape of the bone, the position of the transducer 24 to receive the wave, and the angle of the ultrasonic wave transmitted from the ultrasonic transmission dedicated transducer 21. However, since this embodiment uses the ultrasonic transmission dedicated transducer 21 having a wide directionality as described above, the ultrasonic wave can be impinged on the cortical bone 10 at the critical angle or an angle close to the critical angle. With this configuration, the leaky surface wave or the surface refracted wave can be surely generated and made to reach at least any one of the plurality of transducers 24.

Figure 3:
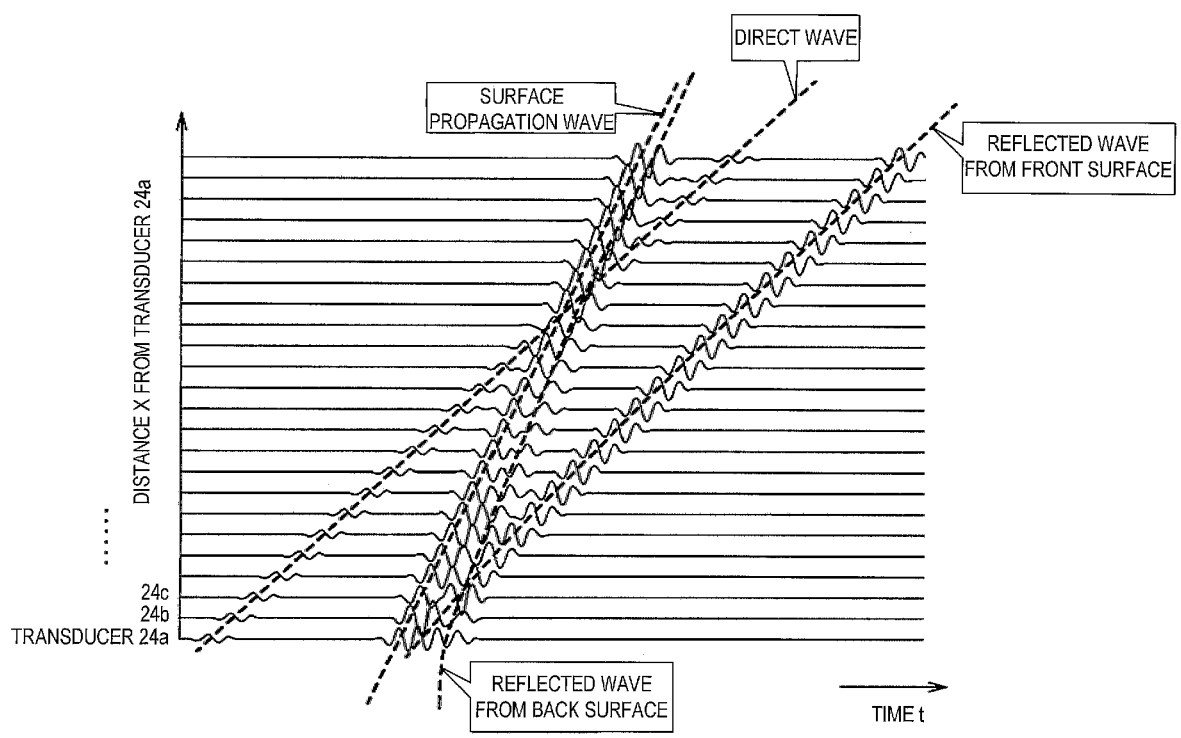
FIG. 3 is a graph illustrating waveform signals outputted by each transducer.

Next, a signal waveform generated by each of the transducers 24 is described with reference to FIG. 3. FIG. 3 is a graph showing a waveform of a signal which is obtained in such a manner in which after the ultrasonic transmission dedicated transducer 21 transmits the ultrasonic wave, each transducer 24 receives the ultrasonic wave and outputs the waveform signal. In the waveform of each transducer 24, an abscissa "t" represents time, and an ordinate of each waveform signal represents an amplitude of the waveform signal. An x-axis represents a distance from the transducer 24a closest to the ultrasonic transmission dedicated transducer 21 to each of the transducers 24b, 24c, etc.

Note that the further the transducer 24 to receive the wave is from the ultrasonic transmission dedicated transducer 21, the smaller the amplitude of the waveform signal. A curve of the waveform shown in FIG. 3 is obtained by giving an adequate gain to the waveform signal to perform an adjustment so that the amplitudes of the individual waveform signals are approximately equalized.

As shown in FIG. 3, the waveform signal of each transducer 24 includes a plurality of peaks. In FIG. 3, points of the peaks included in the waveform signal of each transducer 24 are connected by a dotted line indicating the peak is caused by the direct wave, the reflected wave from the front surface, the reflected wave from the back surface and the surface propagation wave. Note that in the graph, the leaky surface wave and the surface refracted wave is difficult to distinguish, thus they are collectively shown as the surface propagation wave.

As can be seen from the graph of FIG. 3, the direct wave reaches the transducer 24 in some cases later than and in other cases earlier than the surface propagation wave. Furthermore, there is a case where the reflected wave from the back surface and the reflected wave from the front surface reach the transducer 24 at substantially the same time as the surface propagation wave. In this case, the peaks of them overlap and are difficult to distinguish. As described above, even if the waveform signal includes a peak therein, it is difficult to determine via which path the ultrasonic wave having the peak has propagated.

Moreover, the soft tissue 11 is mixed of fat and water, therefore, an unnecessary echo is detected in an actual measurement. In this case, the waveform of FIG. 3 is further added with noise, leading to further difficulty in detecting the peak stably.

Here, the conventional speed-of-sound measurement apparatus as described above has found the bone speed-of-sound by measuring the time interval from the time of transmitting the ultrasonic wave to the time of receiving the surface propagation wave. Therefore, the conventional speed-of-sound measurement apparatus is also necessary to detect the peak of the surface propagation wave; however, as described above, it is difficult to stably detect the peak of the surface propagation wave. Thus, the bone speed-of-sound has not been able to be stably measured by the method of related art.

Consequently, this embodiment achieves the speed-of-sound measurement method resistant to noise by integrating the waveforms of the waveform signals outputted by the plurality of transducers 24.

That is, if the peak positions of plural waveforms coincide, integrating the waveforms results in large amplitudes at the peak positions. By using the aforementioned property, a desired peak only can be emphasized to make the noise less noticeable. However, since timings when the waves reach each of the transducers 24 are variously different, in order for the peaks, based on certain waves are made to heighten each other, it is necessary to shift the phase of each waveform and integrate the waveforms to each other so that the relevant peaks coincide.

Figure 4:
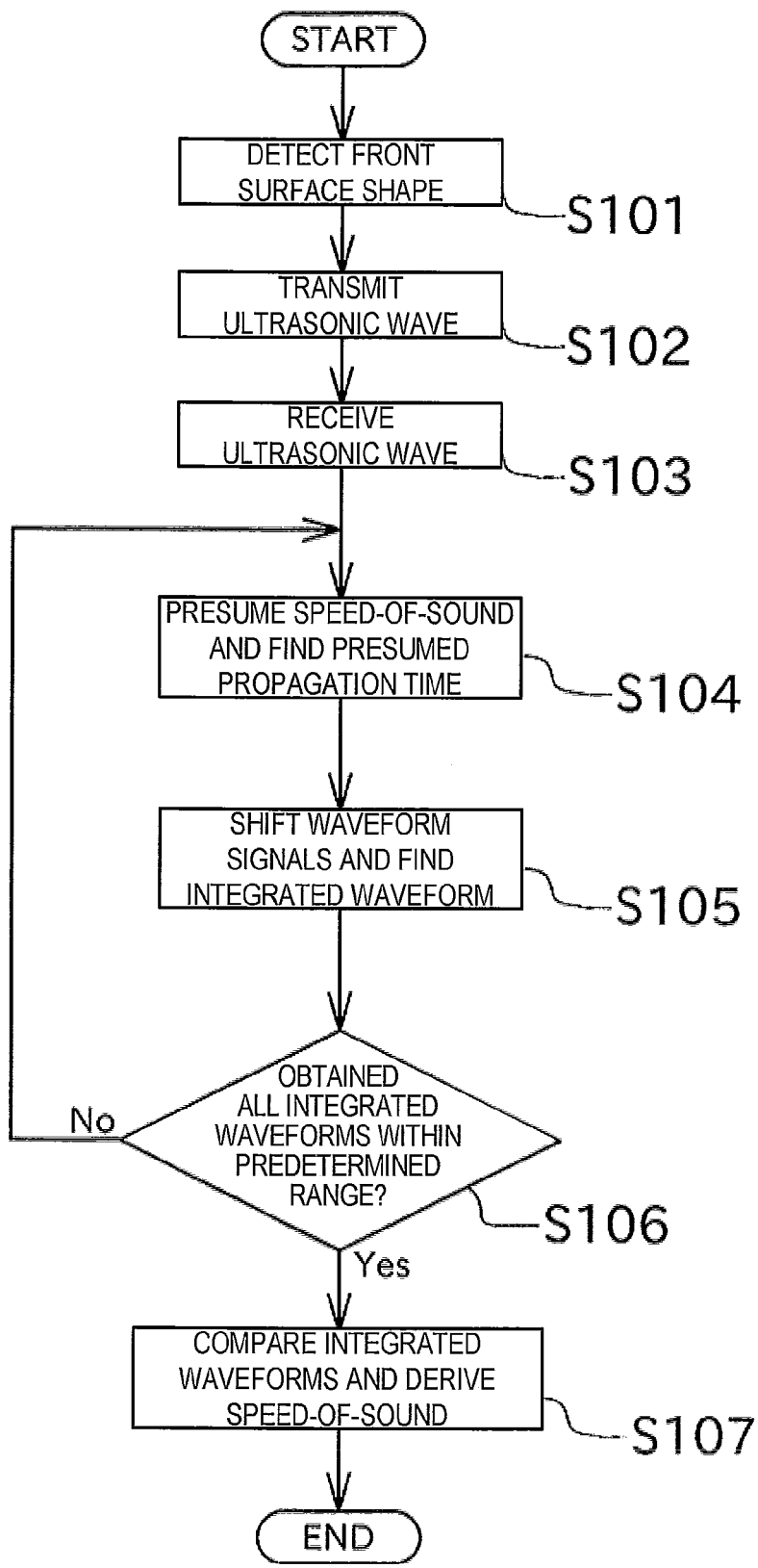
FIG. 4 is a flowchart of a method for measuring speed-of-sound according to this embodiment.

Hereinafter, the speed-of-sound measurement method of this embodiment is specifically described. FIG. 4 shows a flowchart of the speed-of-sound measurement method according to this embodiment. The speed-of-sound measurement method of this embodiment includes a shape detecting step, a wave transmitting step, a wave receiving step, a presumed propagation time calculating step, a waveform integrating step and a speed-of-sound deriving step.

In the shape detecting step, a front surface shape of the cortical bone 10 is measured (S101). The front surface shape may be measured using, for example, an X-ray and the like, but in this embodiment, the front surface shape of the cortical bone 10 is measured by the bone strength diagnostic apparatus 1. Note that the measurement of the front surface shape is described later in detail.

In the wave transmitting step, the ultrasonic wave is transmitted by the ultrasonic transmission dedicated transducer 21 to the cortical bone 10 (S102).

In the wave receiving step, the ultrasonic wave transmitted from the ultrasonic transmission dedicated transducer 21 is received by each of the transducers 24 (S103) to obtain the waveform signal as shown in FIG. 3. As shown in FIG. 3, the peak of the surface propagation wave received by each transducer 24 is detected with more delay, as the position of the relevant transducer 24 becomes far from the ultrasonic transmission dedicated transducer 21. An amount of the delay corresponds to the period of time from when the ultrasonic transmission dedicated transducer 21 transmits the ultrasonic wave to when each transducer 24 receives the surface propagation wave (propagation time).

Therefore, each waveform signal is made to emit earlier by the propagation time of the surface propagation wave (each waveform signal is made to offset to the left side in FIG. 3) to be able to match the peak phases of the surface propagation waves between the transducers 24. However, the bone speed-of-sound is unknown, and thus the propagation time cannot be known in advance.

Therefore, in this embodiment, at the presumed propagation time calculating step, the bone speed-of-sound is presumed, and a presumed value (presumed propagation time) of the propagation time for each transducer 24 is found based on the presumed bone speed-of-sound (speed-of-sound presumed value) and the front surface shape of the cortical bone 10 detected at the shape detecting step (S104).

Next, in the waveform integrating step (validity index value calculating step), the respective waveform signals are offset by the time corresponding to the presumed propagation time, and the waveform signals are integrated to obtain the integrating waveform (S105). At this time, amplitude of an envelope of the integrated waveform is found as a validity index value indicating a validity of the presumed propagation time (described later in detail).

Then, the speed-of-sound presumed value is made to vary in order in a predetermined range to find the integrated waveform for every speed-of-sound presumed value (loop from S104 to S106). Consequently, when the speed-of-sound presumed value matches the actual bone speed-of-sound, the peak phases of the surface propagation waves of the respective wave forms coincide with each other to obtain the integrated waveform with the peaks being most heightened.

Therefore, at the speed-of-sound deriving step, a comparison is performed for the amplitudes of the envelopes of the integrated waveforms found for the plurality of speed-of-sound presumed values to detect the time when the integrated waveform has the largest amplitude and determined the speed-of-sound presumed value at that time as a measurement value of the bone speed-of-sound (S107).

According to the above method, the wave with the peak phases not coinciding (i.e., noise other than the peak of the surface propagation wave) does not highly affect the amplitude of the integrated waveform, and thus, only the surface propagation wave is emphasized (the surface propagation wave may be focused on) to accurately obtain the bone speed-of-sound.

Next, description is given of a configuration for achieving the above speed-of-sound measurement method by the bone strength diagnostic apparatus 1 of this embodiment.

The calculation module 35 included in the apparatus main body 3 of the bone strength diagnostic apparatus 1 shown in FIG. 1 is configured to include hardware such as a CPU, a RANI, and a ROM, and a software such as a program stored in the ROM. The relevant calculation module 35 is configured to function as a shape detecting module 40, a speed-of-sound detecting module 50 and the like in cooperation with the hardware and the software.

First, the shape detecting module 40 is described. The shape detecting module 40 detects a front surface shape of bone required for deriving the speed-of-sound.

That is, when finding the presumed propagation time from the presumed bone speed-of-sound (speed-of-sound presumed value), information about the propagation path of the surface propagation wave is needed. Here, it is necessary to obtain the front surface shape of the cortical bone 10 (section contour shape of the cortical bone 10) in some way in order to find the propagation path. Therefore, in this embodiment, before finding the bone speed-of-sound by the speed-of-sound detecting module 50, the front surface shape of the cortical bone 10 is detected by the shape detecting module 40.

Figure 5A:
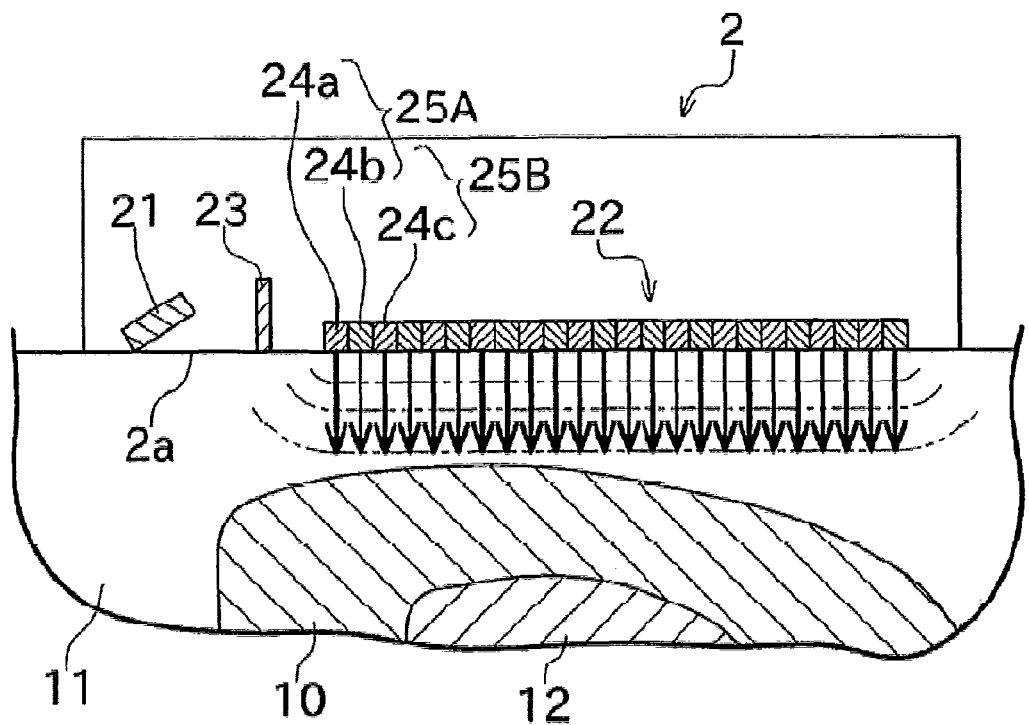
FIG. 5A shows a situation where a plane wave is transmitted by an array transducer.
Figure 5B:
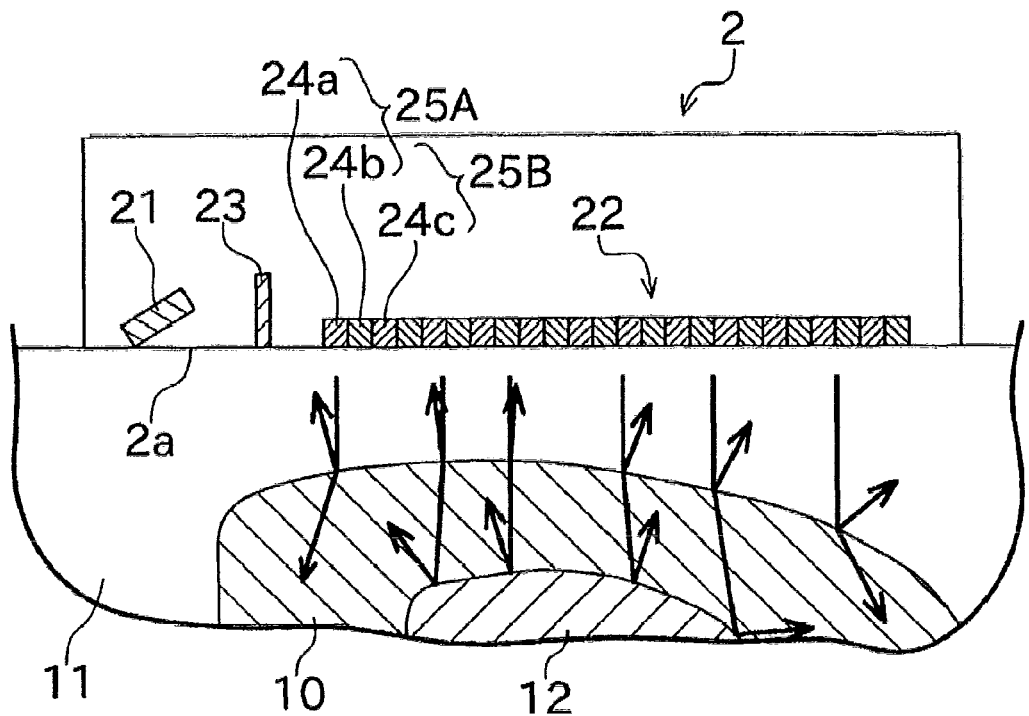
FIG. 5B shows a situation where the plane wave transmitted by the array transducer is reflected on a front surface or a back surface of a cortical bone.

When detecting the front surface shape of bone by the shape detecting module 40, first, the ultrasonic wave is transmitted from the array transducer 22. The situation where the ultrasonic wave is transmitted from by the array transducer 22 is described with reference to FIGS. 5A and 5B. FIG. 5A is a diagram showing a situation where the array transducer 22 transmits the ultrasonic wave. FIG. 5B is a diagram showing a situation where the ultrasonic wave transmitted by the array transducer 22 is reflected on the front surface or the back surface of the cortical bone 10.

In the case of transmitting the ultrasonic wave by the array transducer 22, the transmission switching module 32 determines the array transducer 22 as the transducer to transmit the ultrasonic wave. Then, the pulse signal from the transmission circuit 31 is sent to the array transducer 22 and the plurality of transducers 24 constituting the relevant array transducer 22 transmit simultaneously the ultrasonic wave of the same phase to the bone.

A plane wave as shown in FIG. 5A can be generated by simultaneously transmitting the wave from the plurality of transducers 24. The plane wave is a wave parallel to the contact face 2a, and travels in the soft tissue 11 in a direction perpendicular to the contact face 2a. The plane wave is reflected on the front or back surface of the cortical bone 10 as shown in FIG. 5B, and received by the transducer 24.

When each transducer 24 receives the ultrasonic wave, the waveform signal corresponding to the ultrasonic wave received by each transducer 24 is sent to the calculation module 35. The calculation module 35 is configured to function as the shape detecting module 40 so as to detect an angle and a time when the reflected wave is detected by the transducer 24 and find the front surface shape of the cortical bone 10 based on the angle and the time.

Specifically, the shape detecting module 40 is configured to include an incoming direction detecting module 41, an arrival time detecting module 42, a surface reflection point detecting module 43, and a bone surface line detecting module 44.

First, the incoming direction detecting module 41 is described. The incoming direction detecting module 41 determines a transducer set 25 of two adjacent transducers as a set among the plurality of transducers 24, and detects an incoming direction of the ultrasonic wave to arrive at each transducer set 25. Note that in the description of the shape detecting module 40 below, the ultrasonic wave which is the plane wave transmitted from the array transducer 22 may be referred to as the surface reflected wave in the case of being reflected on the front surface of the cortical bone 10 and received, and similarly referred to as the back surface reflected wave in the case of being reflected on the back surface of the cortical bone 10 and received. Further, respective to each transducer set 25, if necessary to be discerned, may be added with an uppercase alphabet at the end of the numeral thereof from the side closer to the ultrasonic transmission dedicated transducer 21, and represented by the transducer set 25A, transducer set 25B, etc.

Figure 6A:
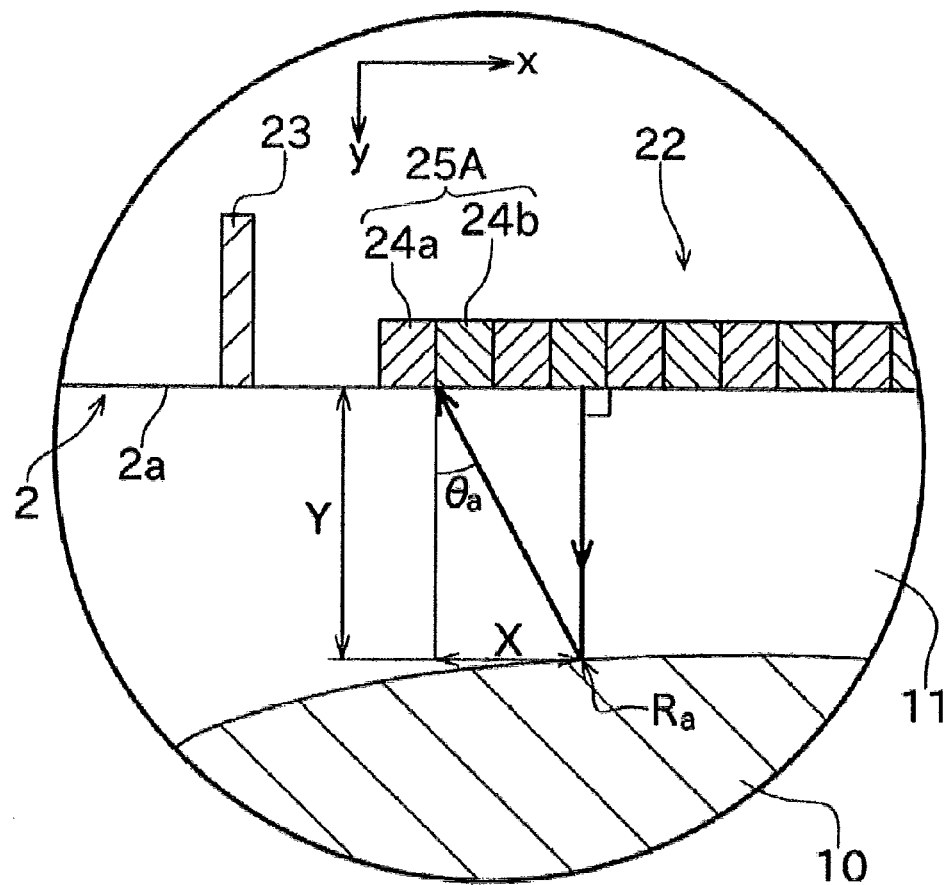
FIG. 6A is a schematic view in which a vicinity of a transducer set receiving a surface reflected wave is enlarged.
Figure 6B:
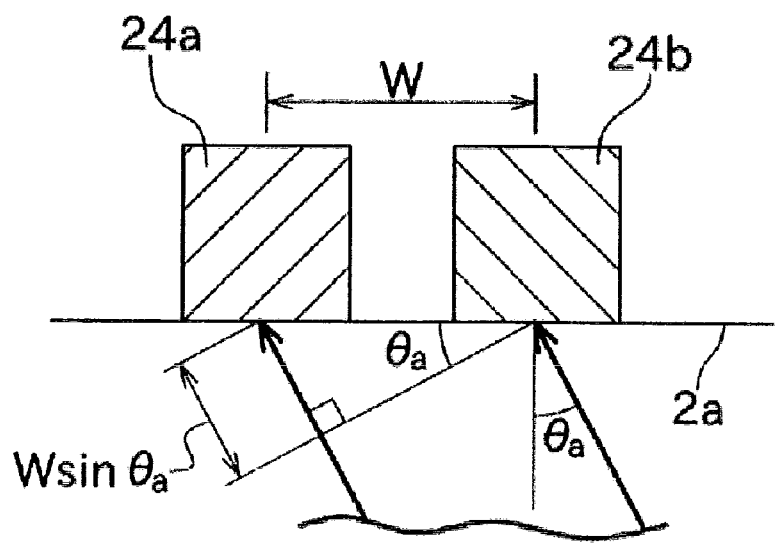
FIG. 6B is a schematic view illustrating a difference between propagation paths of the surface reflected waves coming to two transducers constituting the transducer set.

Hereinafter, a description is given specifically with reference to FIGS. 6A and 6B. FIG. 6A is an enlarged schematic view in the vicinity of the transducer set 25A receiving the surface reflected wave. FIG. 6B is a schematic view illustrating a difference between the propagation paths of the surface reflected waves coming to two transducers 24a and 24b constituting the transducer set. In the certain transducer set 25, the incoming directions of the surface reflected waves for the adjacent two transducers 24 are approximate. For example, in FIGS. 6A and 6B, it can be considered the surface reflected waves respectively come to the transducer 24a and the transducer 24b constituting the transducer set 25A at an incoming angle θa. Here, the following calculation is performed to find the incoming angle θa.

First, the incoming direction detecting module 41 measures a time difference Δt between times when the two transducers 24a and 24b constituting the transducer set 25A respectively detect the peak of the surface reflected wave. Note that when the plane wave is transmitted from the array transducer 22, the front surface reflected wave and the back surface reflected wave are generated as described above; however, the front surface reflected wave is received inevitably earlier than the back surface reflected wave. Therefore, the peak of the surface reflected wave can be adequately detected (thus, the front surface reflected wave is herein simply referred to as "surface reflected wave").

Subsequently, the incoming angle θa of the surface reflected wave for the relevant transducer set 25A is found based on the time difference Δt. As shown in FIG. 6B, on the assumption in which a distance between the transducer 24a and the transducer 24b is W, the surface reflected wave propagates through a distance longer by W sin θa than to the transducer 24b to arrive at the transducer 24a. Here, if the speed-of-sound in the soft tissue is represented by SOSsoft, $$SOSsoft \Delta t = W \sin \theta a$$

Therefore, the coming angle θa can be found by $$\theta a = \arcsin(SOSsoft \Delta t / W).$$

The incoming direction detecting module 41 similarly finds incoming angles for other transducer sets 25. Note that in this embodiment the speed-of-sound SOSsoft in the soft tissue 11 is assigned with a value empirically obtained, but an actual measured value may be assigned.

Next, the arrival time detecting module 42 is described. The arrival time detecting module 42 finds an arrival time Ta, which is a period of time from when the ultrasonic wave is transmitted by the array transducer 22 to when the surface reflected wave arrives at the transducer set 25. In this embodiment, the arrival time Ta is set to an average value of period of time from when the ultrasonic wave is transmitted by the array transducer 22 to when the surface reflected wave arrives at respectively two transducers 24 constituting the transducer set 25. Note that the arrival time Ta is not limited to the average value and may be set to, for example, a time until when the surface reflected wave arrives at either one of the transducers 24.

Next, the surface reflection point detecting module 43 is described. The surface reflection point detecting module 43 detects a reflection point Ra of the surface reflected wave arriving at each transducer set 25 based on the incoming angle θa and the arrival time Ta.

Here, in a plane shown in FIGS. 6A and 6B it is assumed a direction in which the array transducer 22 is arranged is an x-axis, and a direction perpendicular to the x-axis is a y-axis. Then, a direction from the transducer set 25A to the reflection point Ra in the x-axis direction is X, and a distance in the y-axis direction is Y. As is obvious from FIGS. 6A and 6B, a propagation distance La of the surface reflected wave is $$La = Y + Y/\cos \theta a.$$

On the other hand, the arrival time Ta and the speed-of-sound SOSsoft in the soft tissue 11 are used to establish $$La = SOSsoft \times Ta.$$

Therefore, the distances X and Y indicating a position of the reflection point Ra can be found by $$Y = SOSsoft \times Ta \times \cos \theta / (1 + \cos \theta), \text{ and}$$

$$X = Y \times \tan \theta = SOSsoft \times Ta \times \sin \theta / (1 + \cos \theta).$$

In this way, the reflection point Ra can be calculated based on the incoming angle θa and arrival time Ta of the plane wave. Then, the surface reflection point detecting module 43 similarly finds the reflection points for other transducer sets 25.

The bone surface line detecting module 44 connects a plurality of reflection points obtained by the surface reflection point detecting module 43 with a straight line or curved line to detect the bone front surface line. The reflection point is a point on the front surface of the cortical bone 10, and thus the bone front surface line represents the front surface shape of the cortical bone 10.

As described above, the front surface shape of the cortical bone 10 (bone front surface line) can be obtained by the shape detecting module 40.

Next, the speed-of-sound detecting module 50 is described. The speed-of-sound detecting module 50 is configured to detect the speed-of-sound (bone speed-of-sound) in the cortical bone 10.

Before the speed-of-sound detecting module 50 detects the bone speed-of-sound, firstly, the shape detecting module 40 detects the bone front surface line (shape detecting step). Consequently, the ultrasonic wave is transmitted by the ultrasonic transmission dedicated transducer 21 (wave transmitting step), and the returned ultrasonic wave is received by the array transducer 22 and the waveform signal is sent to the calculation module 35 (wave receiving step). Then, based on the waveform signal of each transducer 24, the bone speed-of-sound is derived by the speed-of-sound detecting module 50.

Specifically, the speed-of-sound detecting module 50 is configured to include a presumed propagation time calculating module 51, a waveform integrating module 52 and a speed-of-sound deriving module 53.

The presumed propagation time calculating module 51 performs an arithmetic processing corresponding to the presumed propagation time calculating step. That is, the presumed propagation time calculating module 51 presumes the bone speed-of-sound and finds a presumed propagation time based on the presumed bone speed-of-sound.

The presumed propagation time calculating module 51 first obtains the propagation path of the surface propagation wave in order to find the presumed propagation time. That is, if the front surface shape of the cortical bone 10, the bone speed-of-sound and the speed-of-sound in the soft tissue 11 are known, the path through which the surface propagation wave propagates from the ultrasonic transmission dedicated transducer 21 to each transducer 24 can be uniquely found by Snell's law known.

Here, as a bone shape used is the bone front surface line detected by the shape detecting module 40. As the bone speed-of-sound, a suitable value (speed-of-sound presumed value) is presumed from a predetermined range set based on empirical values of the bone speed-of-sound and used for calculation. In this embodiment, the empirical value is used as the speed-of-sound in the soft tissue 11, but a value measured in advance may be used. Further, the speed-of-sound in the soft tissue 11 can be measured by transmitting the ultrasonic wave by the ultrasonic transmission dedicated transducer 21 or the array transducer 22, and receiving the wave by the array transducer 22.

Note that as described above, the surface propagation wave received by each transducer 24 has two kinds of waves, the leaky surface wave and the surface refracted wave, due to the difference in the propagation path. In this embodiment, the description is given with the assumption the propagation path of the surface refracted wave is calculated.

Figure 7:
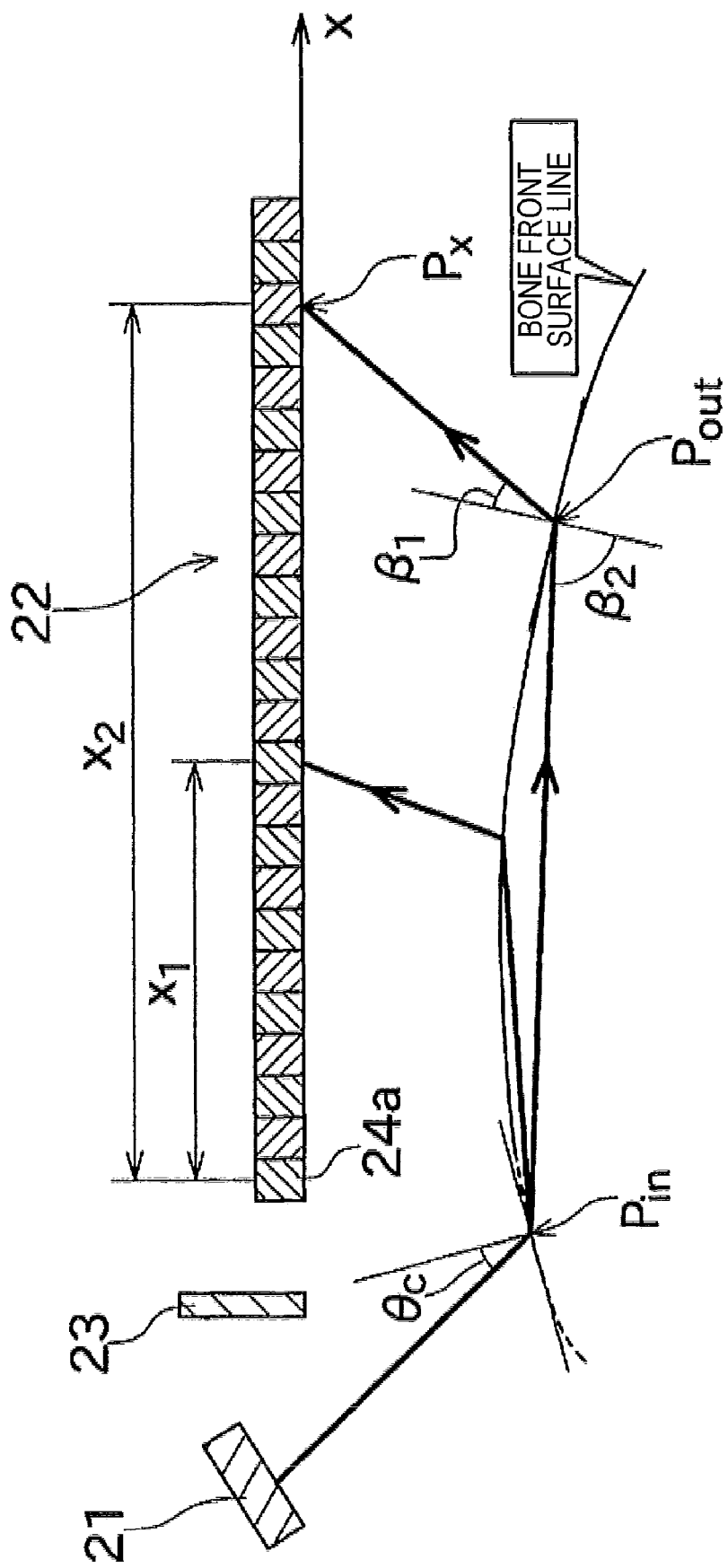
FIG. 7 is a schematic view illustrating a calculation method of the propagation path of the surface refracted wave.

Hereinafter, a description is given with reference to FIG. 7. FIG. 7 is a schematic view illustrating a calculating method for the propagation path of the surface refracted wave.

The presumed propagation time calculating module 51 firstly determines an incident point Pin at which the ultrasonic wave from the ultrasonic transmission dedicated transducer 21 enters the inside of the cortical bone 10 in order to determine the propagation path of the surface refracted wave.

Note that since the incident point Pin is located outside a position immediately below the array transducer 22, the front surface shape in the vicinity of the relevant incident point Pin cannot be obtained in a method for detecting the surface reflected wave by transmitting the plane wave from the array transducer 22 (detection of the front surface shape of the cortical bone by the shape detecting module 40). Consequently, this embodiment presumes the shape in the vicinity of the incident point Pin based on the bone front surface line obtained by the shape detecting module 40. FIG. 7 shows the presumed bone front surface line with a dashed line.

Next, the presumed propagation time calculating module 51 finds a position where the ultrasonic wave enters with respect to the presumed line (incident point Pin). The ultrasonic wave can enter the inside of the cortical bone 10 at arbitrary angles smaller than the critical angle θc. However, the case where the surface refracted wave is received by the transducer 24 is limited to a case where the ultrasonic wave enters the inside of the cortical bone 10 at an angle closer to the critical angle θc. Thus, in this embodiment, an incident position is approximately found with the assumption the ultrasonic wave enters the inside of the cortical bone 10 at the critical angle θc. Since the critical angle θc is determined depending on the bone speed-of-sound and the speed-of-sound in the soft tissue, the incident point Pin can be uniquely found by presuming the bone speed-of-sound.

Subsequently, the presumed propagation time calculating module 51 sets an arbitrary point Pout on the bone front surface line. A distance in a straight line from the incident point Pin to the point Pout is the distance through which the ultrasonic wave propagates in the cortical bone 10.

Then, the presumed propagation time calculating module 51 finds an angle at which the ultrasonic wave is emitted from Pout to the soft tissue 11 side. The angle at which the ultrasonic wave is emitted can be uniquely found by Snell's law. Specifically, on the assumption the speed-of-sound presumed value is SOSbone, and the speed-of-sound in the soft tissue is SOSsoft, a relationship between an refraction angle β1 and an incident angle β2 when the ultrasonic wave is emitted from the cortical bone 10 to the soft tissue 11 side is $\sin \beta 1 / SOS\text{soft} = \sin \beta 2 / SOS\text{bone}.$ The incident angle β2 can be found from an inclination of a straight line Pin-Pout and the shape of the bone front surface line. Therefore, the refraction angle β1 can be found from the above formula.

Here, as shown in FIG. 7, a direction in which the array transducer 22 is arranged is taken as the x-axis with an origin thereof at a position of the transducer 24a; the closest to the ultrasonic transmission dedicated transducer 21. The shapes of the refraction angle β1 and bone front surface line are known, therefore, determined is a point Px at which the ultrasonic wave emitted from the point Pout intersects with the x-axis. With the arithmetic processing described above, the propagation path of the surface refracted wave from the ultrasonic transmission dedicated transducer 21 to the point Px can be found.

Note that the purpose of assuming the ultrasonic wave enters the inside of the cortical bone 10 approximately at the critical angle θc when finding the incident point Pin is to facilitate the calculation, and the propagation path calculated has an approximate value. On the other hand, the propagation path can be strictly calculated without the angle of incident on the cortical bone 10 being approximated at the critical angle θc. Specifically, if the front surface shape of the cortical bone 10 is known, the propagation path from the ultrasonic transmission dedicated transducer 21 to the point Px can be strictly calculated using Snell's law two times with the angle of incident on the cortical bone 10 being varied. In this case, the incident point Pin varies depending on the point Px. However, the strict calculation of the propagation path like the aforementioned takes a longer processing time compared with the calculation method in which the incident angle is approximated at the critical angle θc. This embodiment is configured to enable the calculation of the propagation path by the method of approximate calculation or strict calculation, one of which is to be selected.

Then, the presumed propagation time calculating module 51 finds the propagation time from when the ultrasonic wave is transmitted by the ultrasonic transmission dedicated transducer 21 to when the surface refracted wave arrives at the point Px based on the found propagation path. That is, the following is established.

Figure 8:
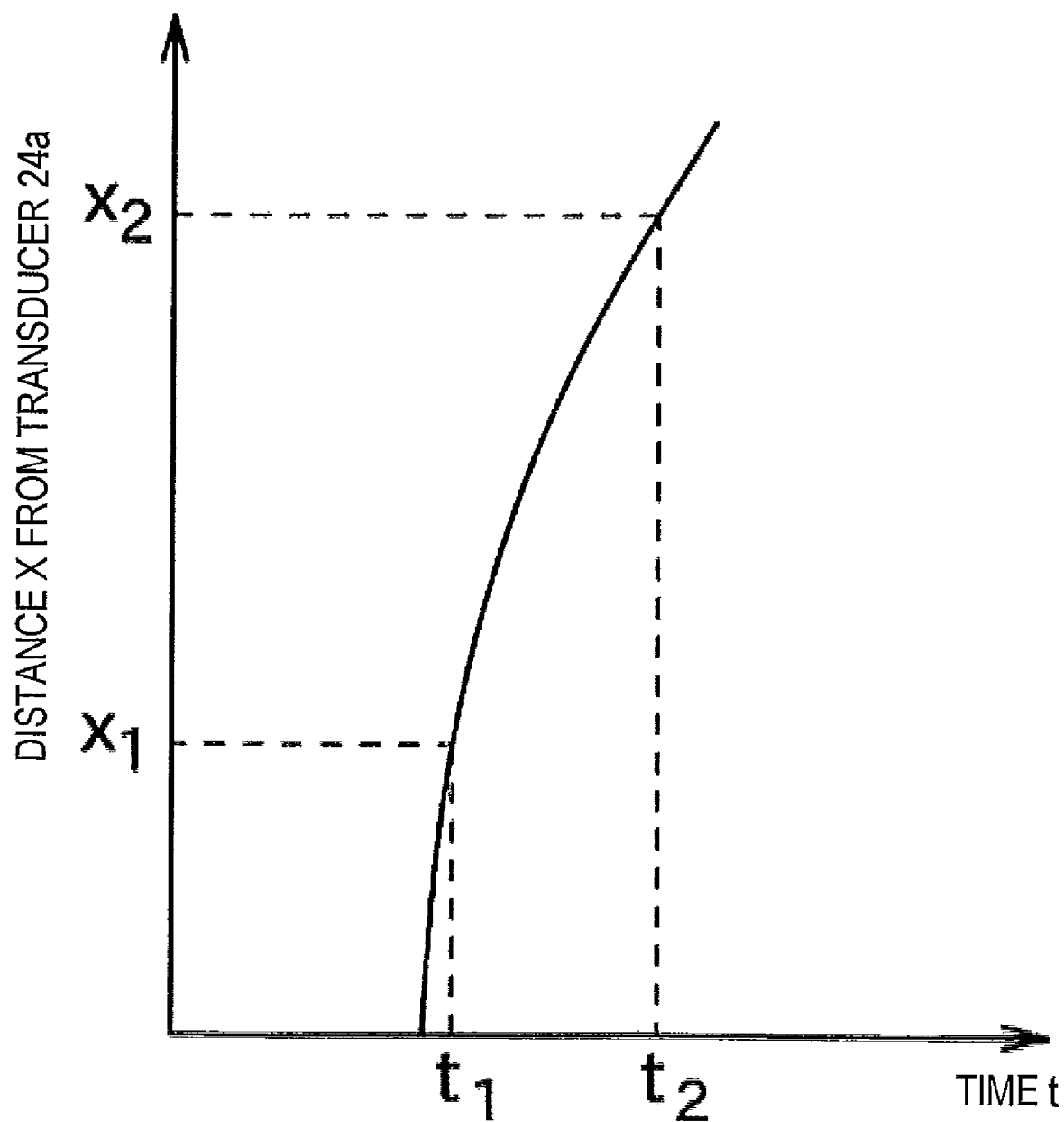
FIG. 8 is a graph showing a t-x curve obtained by a presumed propagation time calculating module.

(The propagation time to the point $Px$)=(The distance propagated in the soft tissue)$\times SOS$soft+(The distance propagated in the cortical bone)$\times SOS$bone The presumed propagation time calculating module 51 repeats the calculation of the above propagation time with the position of Pout being varied. This makes the propagation times of the surface refracted wave to the respective points Px found with the position of the point Px being varied, enabling a t-x curve as shown in FIG. 8 to be found. Note that the ordinate axis "x" in FIG. 8 represents the distance from the transducer 24a, and the abscissa axis "t" represents the propagation time from when the ultrasonic transmission dedicated transducer 21 transmits the ultrasonic wave to when the surface refracted wave arrives at the x-axis.

Finally, the presumed propagation time calculating module 51 finds a time taken until the surface refracted wave arrives (presumed propagation time) at each transducer 24. Specifically, an x-coordinate of each transducer 24 (distance from the transducer 24a) is known, thus the presumed propagation time for each transducer 24 can be found by referring to the t-x curve.

Next, the waveform integrating module 52 is described. The waveform integrating module 52 (validity index value calculating module) performs an arithmetic processing corresponding to the waveform integrating step. Specifically, the waveform integrating module 52 is configured to shift (offset) the waveform of the waveform signal output from each transducer 24 by the presumed propagation time to be integrated, and find the integrated waveform.

Figure 9:
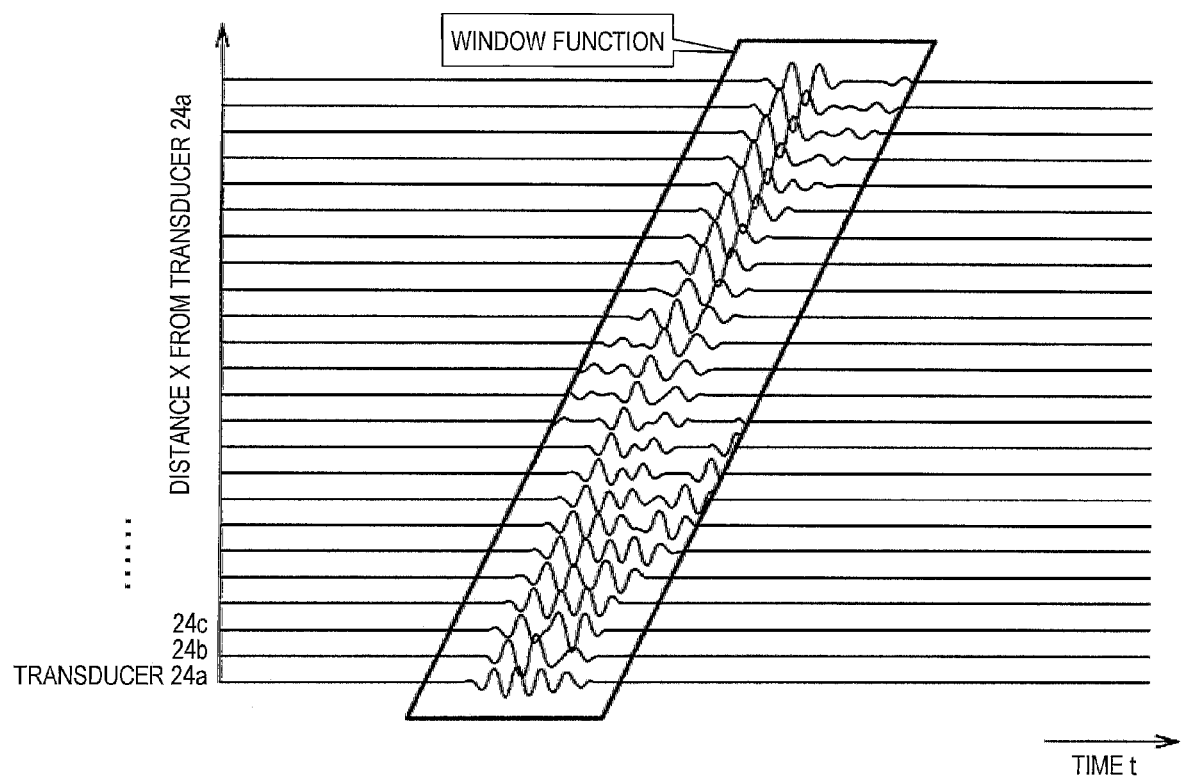
FIG. 9 is a graph showing a case where the waveform signal of each transducer is multiplied by a window function.

Hereinafter, a description is made specifically. First, the waveform integrating module 52, before integrating the waveform signal, multiply the waveform signal by a suitable window function in order to eliminate the wave except for the surface refracted wave (FIG. 9). Note that it is necessary to know the bone speed-of-sound and the propagation time to some extent to determine a range of the window function. However, even if all of the waves except for the surface refracted wave cannot be eliminated by the window function, effects of the remained waves can be lowered with the waveform signals being integrated to each other. Therefore, the window function is not necessarily to be strictly determined in order to eliminate all the waves except for the surface refracted wave. Consequently, the window function may be enough so long as it is determined with an adequate margin taken into consideration based on the bone speed-of-sound, the empirical value of the speed-of-sound in the soft tissue 11 and the like.

Moreover, the further the transducer 24 is from the ultrasonic transmission dedicated transducer 21, the weaker the amplitude of the waveform signal. Therefore, the waveform integrating module 52 gives an adequate gain to the waveform signal of each transducer 24 to adjust the respective waveform signals so as to have the same amplitudes. Here, the gain may be given by a method which is determined based on the maximum amplitude of the waveform signal obtained with the window function or determined with presumption of decay of an adequate exponential function.

Figure 10:
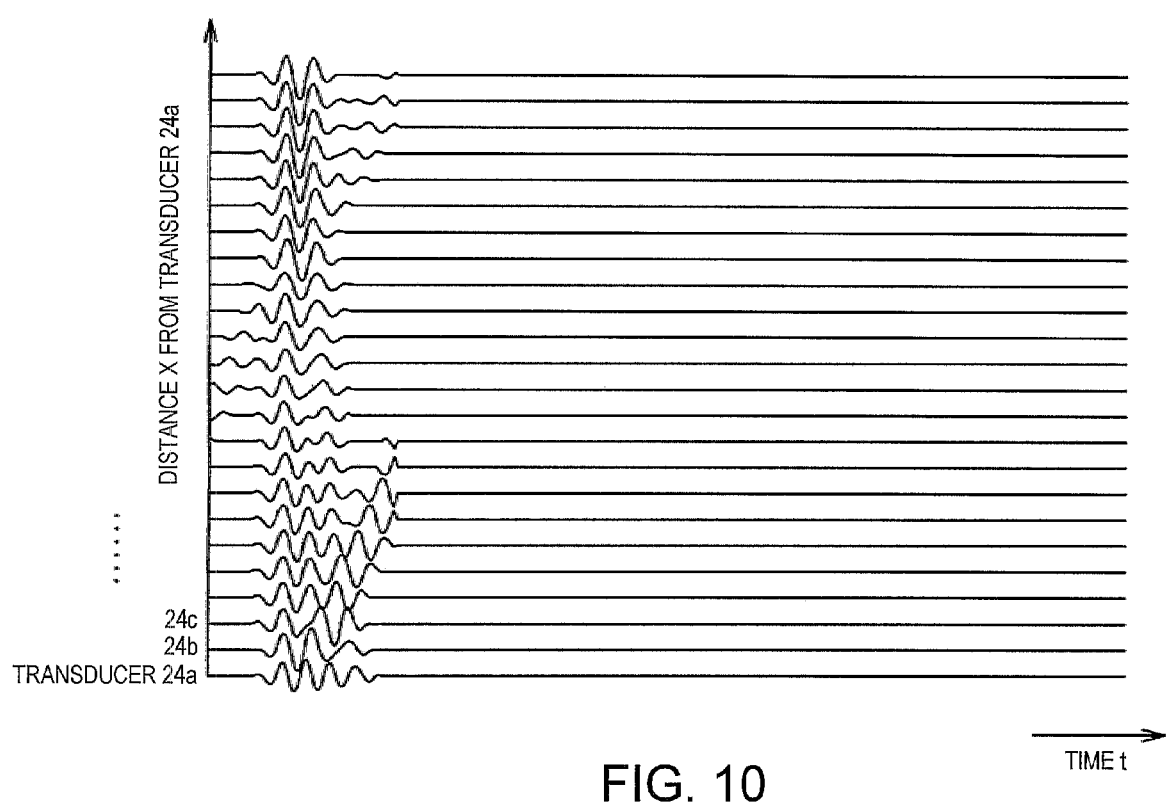
FIG. 10 is a graph showing a case where the waveform signal of each transducer is shifted.

Subsequently, the waveform integrating module 52 shifts each waveform signal adjusted by being multiplied by the window function and the gain by a time corresponding to the presumed propagation time of each transducer 24 so the time is set ahead (i.e., offsetting to the left in FIG. 9). The respective waveform signals, if shifted, become as is shown in FIG. 10, for example. Note that the peak phases of the surface refracted waves included in the respective waveform signals coincide in FIG. 10. In this way, the peaks coincide as the result of shifting the waveform signal when the speed-of-sound presumed value matches the actual bone speed-of-sound.

Figure 11:
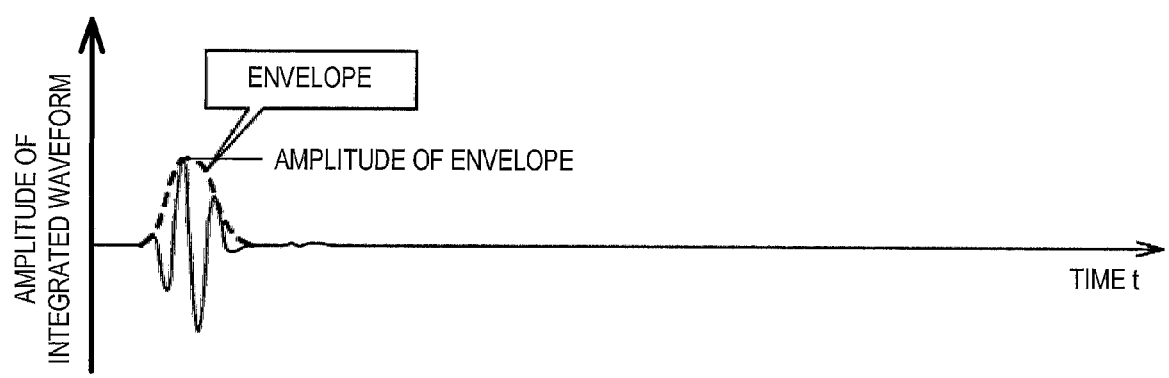
FIG. 11 is a graph showing an integrated waveform obtained by a waveform integrating module.

Then, the waveform integrating module 52 integrates the shifted waveform signals with each other to find the integrated waveform as shown in FIG. 11.

Finally, the waveform integrating module 52 creates the envelope of the integrated waveform to find an amplitude of the envelope (see FIG. 11). As is described later, the amplitude of the envelope is an index representing whether or not the peaks of the surface propagation wave after offset coincide (specifically, whether or not the presumed propagation time matches the actual bone speed-of-sound). That is, the amplitude of the envelope is a validity index value indicating a validity of the presumed propagation time.

Next, the speed-of-sound deriving module 53 is described. The speed-of-sound deriving module 53 is configured to repeat a process (loop process) for calling functions of the presumed propagation time calculating module 51 and the waveform integrating module 52 to find the amplitude of the envelope.

Figure 12:
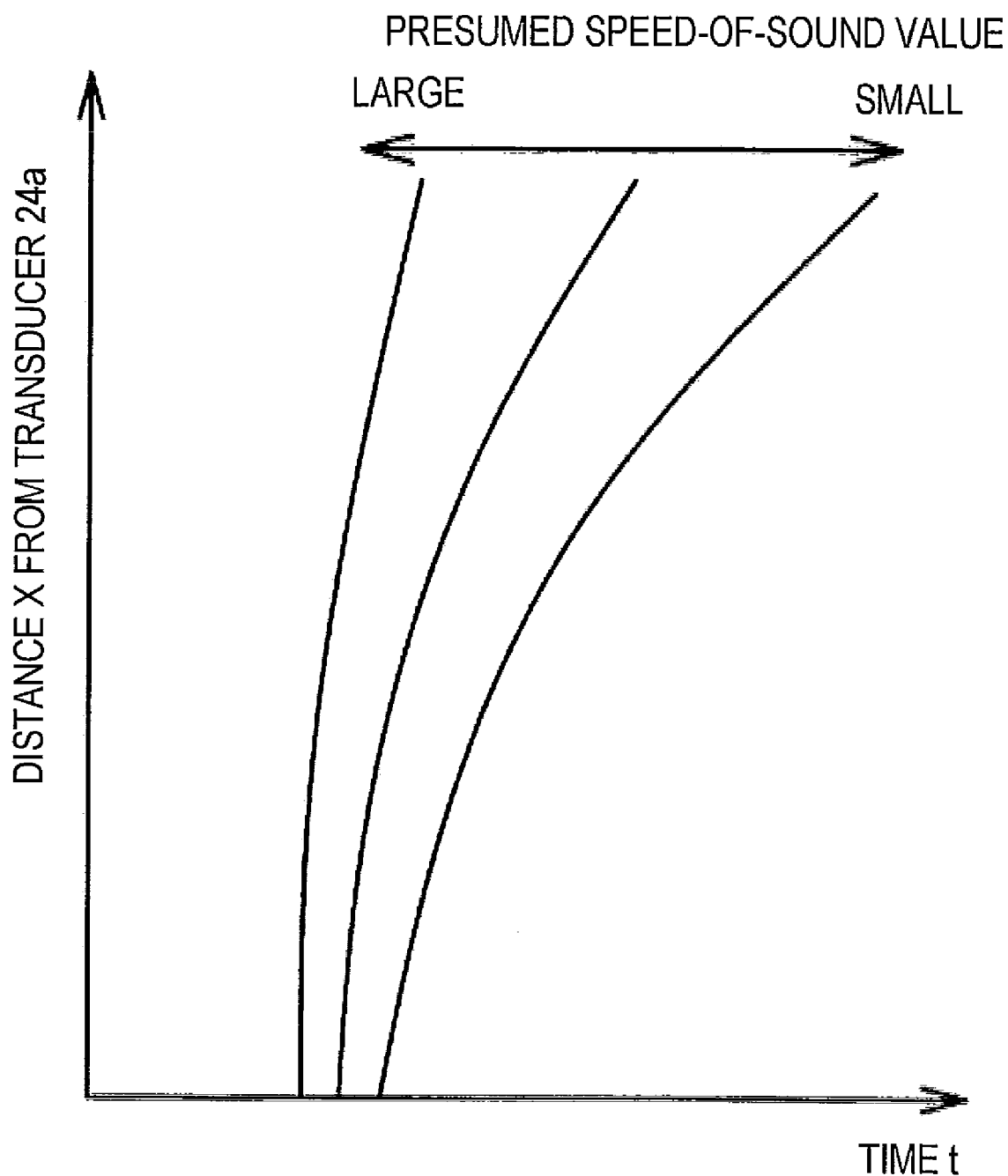
FIG. 12 is a graph showing the t-x curve with a speed-of-sound presumed value being varied.

In the loop process performed at the speed-of-sound deriving module 53, the presumed propagation time calculating module 51 calculates the presumed propagation time using the speed-of-sound presumed value different from the one used previous time every time called. Specifically, the presumed propagation time calculating module 51 uses a new speed-of-sound presumed value in every loop to find a new t-x curve. For example, the plurality of t-x curves found with the speed-of-sound presumed values being varied are shown in FIG. 12. As shown in the graph of FIG. 12, if the speed-of-sound presumed value is different, the inclination of the t-x curve, the intersection of the relevant t-x curve and the t coordinate axis and the like are varied. Therefore, if the speed-of-sound presumed value is different, an amount of shifting the waveform signal in integrating the waveform signal is different.

Figure 13:
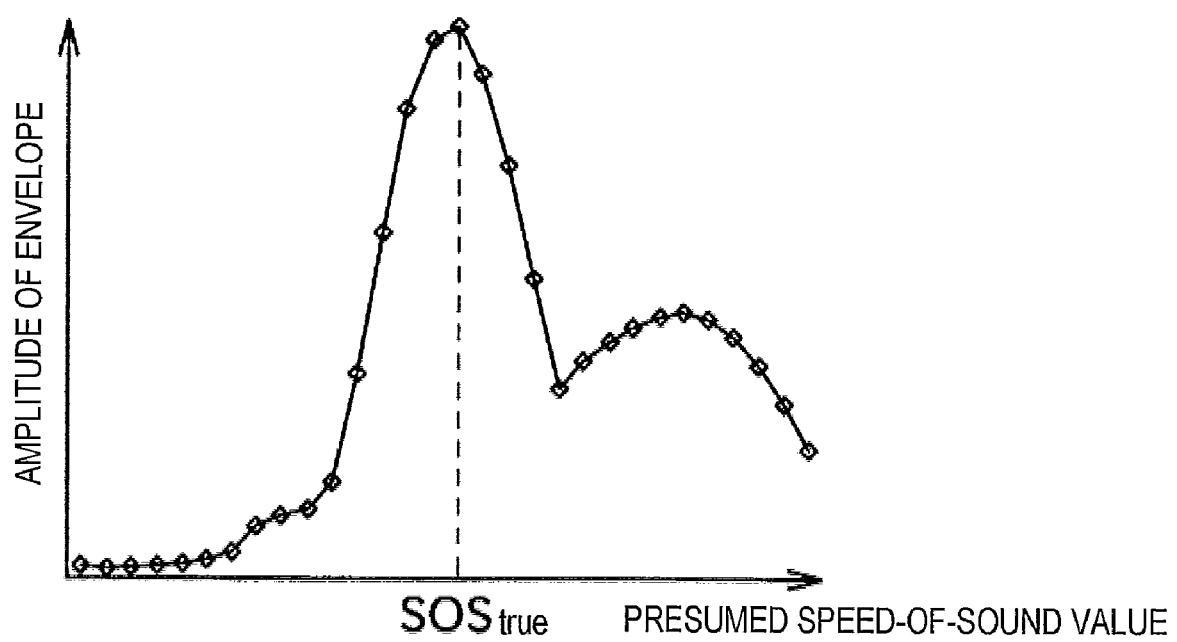
FIG. 13 is a graph showing an example result of amplitude of an envelope is found and plotted with the speed-of-sound presumed value being varied.

When the amount of shifting each waveform signal is varied, the integrated waveform is varied. Therefore, by varying the speed-of-sound presumed value, the amplitude of the envelope is varied. The speed-of-sound deriving module 53 repeats the loop with the speed-of-sound presumed value being varied in a predetermined range to find the amplitude values of the envelopes in all the cases in the predetermined range. FIG. 13 shows an example of results of plotting the amplitudes of the envelopes which are obtained by varying the speed-of-sound presumed value in this way.

In the example in FIG. 13, when the presumed speed-of-sound is SOStrue, the amplitude of the envelope is the maximum. That is, it is considered when the presumed speed-of-sound is SOStrue, the peaks of the surface refracted waves included in the respective waveform signals are most heightened with each other (the peak phases of the surface refracted waves coincide as shown in FIG. 10). Consequently, the speed-of-sound deriving module 53 employs the SOStrue as the measurement value of the speed-of-sound. As described above, the speed-of-sound deriving module 53 performs the arithmetic processing corresponding to the speed-of-sound deriving step to derive the speed-of-sound.

Figure 14:
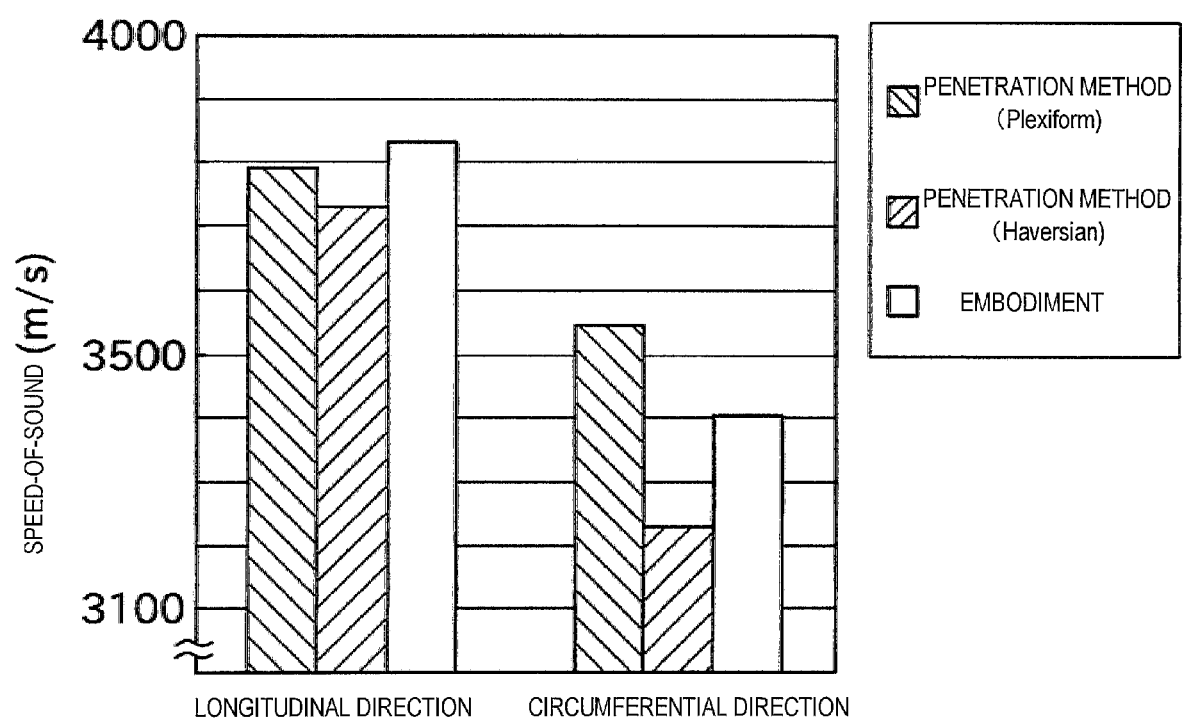
FIG. 14 shows a result of measurement of speed-of-sound in a bovine tibia cortical bone using a bone strength diagnostic apparatus according to this embodiment.

Next, a description is given of an example in which the bone speed-of-sound is actually measured by the speed-of-sound measurement method using the above bone strength diagnostic apparatus 1. The present inventors measured the speed-of-sound of a bovine tibia cortical bone using the above bone strength diagnostic apparatus 1 in order to confirm effectiveness of the above speed-of-sound measurement method. Additionally, in order to evaluate whether or not results thereof were correct, the comparison with the measurement value by the bone strength diagnostic apparatus 1 was performed in such a way the relevant bovine tibia was cut out to form into a block like and measure the speed-of-sound thereof in the longitudinal direction and in the circumferential direction by a penetration method. The result thereof is shown in FIG. 14.

First, a description is given of the results of the measurement of the speed-of-sound by the penetration method. It is known for the bovine bone to have a Haversian structure made of osteon and a lamellar Plexiform structure. Note that as a result of an observation using a microscope, it was found there existed the Plexiform structure outside the cortical bone in many locations and the Haversian structure inside the cortical bone in many locations. Consequently, in the penetration method, the speed-of-sounds in the circumferential direction and the longitudinal direction were measured for the Plexiform structure and the Haversian structure, respectively.

Note that the long bone which is often exposed to a load in a longitudinal direction is generally strengthened in the longitudinal direction. Therefore, the speed-of-sound generally is larger in the longitudinal direction than in the circumferential direction. As shown in FIG. 14, the result was obtained in which the speed-of-sound in the longitudinal direction is larger than in the circumferential direction in the measurement by the penetration method.

Next, a description is given of the results of the measurement of the speed-of-sound using the bone strength diagnostic apparatus 1 of this embodiment. As shown in FIG. 14, the speed-of-sound in the longitudinal direction obtained using the bone strength diagnostic apparatus 1 of this embodiment substantially matches the results of the measurement by the penetration method. Moreover, the results of the measurement of the speed-of-sound in the circumferential direction using the bone strength diagnostic apparatus 1 of this embodiment had an average-like value of values of the Plexiform structure and the Haversian structure. Therefore, it was confirmed the bone speed-of-sound can suitably be measured using the bone strength diagnostic apparatus 1 of this embodiment. Note that it is said a human bone in most parts in general is formed of the Haversian structure. Therefore, the bone speed-of-sound in the human bone can be considered to be suitably measured using the bone strength diagnostic apparatus 1.

As described above, the bone strength diagnostic apparatus 1 of this embodiment includes the ultrasonic transmission dedicated transducer 21, the plurality of transducers 24, the presumed propagation time calculating module 51, the waveform integrating module 52 and the speed-of-sound deriving module 53. The ultrasonic transmission dedicated transducer 21 transmits the ultrasonic wave to the front surface of the cortical bone 10. The transducer 24 receives the ultrasonic wave from the cortical bone 10, and outputs the waveform signal depending on the received ultrasonic wave. The presumed propagation time calculating module 51 calculates the propagation time from when the ultrasonic wave is transmitted by the ultrasonic transmission dedicated transducer 21 to when the ultrasonic wave arrives at each transducer 24 after propagating in the vicinity of the front surface of the cortical bone 10 based on the presumed value of speed-of-sound in the relevant cortical bone 10 and the front surface shape of the relevant cortical bone 10. The waveform integrating module 52 finds the amplitude of the envelope of the integrated waveform as the index of the validity of the propagation time based on the waveform signals outputted by at least two of the plurality of transducers 24. The speed-of-sound deriving module 53 finds the speed-of-sound in the cortical bone 10 based on the amplitude of the envelope of the integrated waveform.

That is, by determining the validity of the presumed propagation time, determination can be made of whether or not the speed-of-sound presumed in calculating the relevant presumed propagation time is correct. This makes it possible to find the speed-of-sound in the cortical bone 10. Here, it is not strictly necessary to detect the position of the peak of the received waveform when determining the validity of the presumed propagation time. Therefore, even if the received waveform includes a noise, the speed-of-sound can be adequately found. Further, the validity of the presumed propagation time is determined based on the waveform signals from the plurality of transducers 24, allowing the effect of the noise to be reduced.

Moreover, in the bone strength diagnostic apparatus 1 of this embodiment, the waveform integrating module 52 shifts respectively the waveform signals outputted by at least two of the plurality of transducers 24 by a time corresponding to the presumed propagation time, and finds the integrated waveform by integrating the shifted waveform signals to each other to find the amplitude of the envelope of the relevant integrated waveform.

Specifically, when the waveform signals outputted by the wave reception modules of the plurality of transducers 24 are integrated to each other, in the case where the peak positions of the waveforms coincide, the amplitudes are most strengthened with each other. By using the aforementioned property, only a desired peak can be emphasized to lower the effects of other noises. With the above configuration, if the speed-of-sound presumed by the presumed propagation time calculating module 51 is correct, the peak positions of the integrated waveform signals coincide to strengthen the amplitudes with each other. Therefore, even if the waveform signal outputted by the transducer 24 includes a noise, determination can be performed whether or not the presumed value of speed-of-sound is correct by observing the integrated waveform.

In addition, the bone strength diagnostic apparatus 1 of this embodiment is configured as follows. That is, the presumed propagation time calculating module 51 calculates the propagation time using plural kinds of speed-of-sound presumed values. The waveform integrating module 52 finds the amplitude of the envelope of the integrated waveform in response to each of the plural kinds of speed-of-sound presumed values. Then, the speed-of-sound deriving module 53 compares the amplitudes of the envelopes of the respective plural kinds of speed-of-sound presumed values with each other to find the speed-of-sound in the cortical bone 10.

This makes it possible for the plural kinds of speed-of-sound presumed values to be tested so that the speed-of-sound presumed value, which has the peaks most strengthened with each other (peak positions most coinciding), can be employed as the measurement value of the bone speed-of-sound.

Furthermore, in the bone strength diagnostic apparatus 1 of this embodiment, the presumed propagation time calculating module 51 calculates the propagation time based on the front surface shape measured in advance of the cortical bone 10.

This makes it possible to calculate the propagation time with the actual front surface shape of the cortical bone 10 taken into consideration, even if, for example, the front surface of the cortical bone 10 is curved, the speed-of-sound thereof can be accurately found.

Furthermore, the bone strength diagnostic apparatus 1 of this embodiment includes the shape detecting module 40. The plurality of transducers 24 are configured to be able to generate the plane wave by simultaneously transmitting the ultrasonic wave to the front surface of the cortical bone 10. The shape detecting module 40 detects the front surface shape of the cortical bone 10 based on an arrival angle at which the plane wave reflected on the front surface of the cortical bone 10 arrives at each transducer 24. Then, the presumed propagation time calculating module 51 calculates the propagation time based on the front surface shape of the cortical bone 10 by being detected by the shape detecting module 40.

This makes it possible to detect the front surface shape of the cortical bone 10 using a part of the configuration for measuring the speed-of-sound, enabling the apparatus to be simplified to reduce the cost.

Further, the speed-of-sound measurement method of this embodiment includes the wave transmitting step (S102), the wave receiving step (S103), the presumed propagation time calculating step (S104), and the waveform integrating step (S105). In the wave transmitting step, the ultrasonic wave is transmitted to the front surface of the cortical bone 10. In the wave receiving step, the ultrasonic wave from the cortical bone 10 is received by each transducer 24. In the presumed propagation time calculating step, calculated is the propagation time from when the ultrasonic wave is transmitted in the wave transmitting step to when the ultrasonic wave arrives at each transducer 24 after propagating in the vicinity of the front surface of the cortical bone 10 based on the presumed value of speed-of-sound in the relevant cortical bone 10 and the front surface shape of the relevant cortical bone 10. In the waveform integrating step, found is the amplitude of the envelope of the integrated waveform as the index of the validity of the propagation time based on the waveform signals outputted by at least two of the plurality of transducers 24. Then, the presumed propagation time calculating step and the waveform integrating step are repeatedly performed with the speed-of-sound presumed value being varied (loop of S104 to S106) to find the integrated waveform for each of the plural kinds of speed-of-sound presumed values. Subsequently, the amplitude of the envelope of the integrated waveform for each kind is compared with one another to find the speed-of-sound in the cortical bone 10 (S107).

That is, whether or not the speed-of-sound presumed in calculating the propagation time is correct can be determined by determining the validity of the propagation time. This makes it possible to find the speed-of-sound in the cortical bone 10. Here, since the peak of the received waveform is not necessary to be strictly detected when determining the validity of the propagation time, the speed-of-sound can be adequately found even if the received waveform includes the noise. Moreover, the validity of the propagation time is determined based on the waveform signals from the plurality of transducers 24, allowing the effects of the noise to be lowered. Then, in the case where the propagation time obtained by testing the plural kinds of presumed values of speed-of-sound is most valid, the presumed value of speed-of-sound when calculating the relevant propagation time can be employed as the measurement value of the speed-of-sound in the subject's body.

Additionally, the speed-of-sound measurement method of this embodiment employs the following methods. Specifically, in the waveform integrating step, the waveform signals outputted by at least two of the plurality of wave reception modules is shifted by a time corresponding to the propagation time, the shifted waveform signals are integrated to each other to find the integrated waveform, and the amplitude of the envelope of the relevant integrated waveform is found.

That is, if the waveform signals by output the plurality of transducers 24 are integrated to each other, the amplitudes are most strengthened when the peak positions of the waveform coincide. By using the aforementioned property, only the desired peak can be emphasized to lower the effects of other noises. In the above configuration, if the speed-of-sound presumed in the presumed arrival time calculating step is correct, the peak positions of the integrated waveform signals coincide to strengthen the amplitudes to each other. Therefore, even if the waveform signal outputted by the transducer 24 includes the noise, whether or not the presumed value of speed-of-sound is correct can be determined by checking the integrated waveform.

Further, the speed-of-sound measuring step of this embodiment includes shape detecting step (S101) for detecting the front surface shape of the cortical bone 10. Then, in the presumed propagation time calculating step, the propagation time is calculated based on the front surface shape.

This makes it possible to calculate the presumed propagation time with the actual shape of the front surface of the cortical bone 10 taken into consideration; therefore, the speed-of-sound can be accurately found even if the front surface shape of the cortical bone 10 is curved, for example.

Next, a description is given of a modified example of the bone strength diagnostic apparatus 1 of the above embodiment.

The bone strength diagnostic apparatus according to this modified example includes a waveform multiplying module as the validity index value calculating module. That is, in the above embodiment, the waveform integrating module 52 as the validity index value calculating module shifts the waveform signal of each transducer 24 in response to the presumed propagation time, and integrates the shifted waveform signal to one another to find the integrated waveform. In this regard, the waveform multiplying module of the modified example is configured to shift the waveform signal of each transducer 24 in response to the presumed propagation time, and multiply the shifted waveform signal by another one to find a multiplied waveform and find the validity index value based on the multiplied waveform.

As described above, the speed-of-sound measurement apparatus according to the modified example, the waveform multiplying module shifts the waveform signals outputted by at least two of the plurality of transducers 24 by a time corresponding to the presumed propagation time, and multiplies the shifted waveform signals by one another to find the multiplied waveform and find the validity index value based on the relevant multiplied waveform.

Further, in the speed-of-sound measurement method using the speed-of-sound measurement apparatus according to the modified example, a waveform multiplying step is performed as the validity index value calculating step in place of the waveform integrating step of the above embodiment. Specifically, in the waveform multiplying step, the waveform signals outputted by at least two of the plurality of wave reception modules are shifted by a time corresponding to the propagation time, the shifted waveform signals are multiplied by one another to find the multiplied waveform and find the validity index value based on the relevant multiplied waveform.

Specifically, if the waveform signals outputted by the wave reception modules of the plurality of transducers 24 are multiplied by one another, the amplitudes are most strengthened when the peak positions of the waveforms coincide. By using the aforementioned property, only the desired peak can be emphasized to lower the effects of other noises. In the above configuration, if the speed-of-sound presumed in the presumed propagation time calculating module 51 is correct, the peak positions of the multiplied waveform signals coincide to strengthen the amplitudes to each other. Therefore, even if the waveform signal outputted by the transducer 24 includes the noise, whether or not the presumed value of speed-of-sound is correct can be determined by observing the multiplied waveform.

Next, a description is given of another modified example of the bone strength diagnostic apparatus 1 of the above embodiment.

Figure 15:
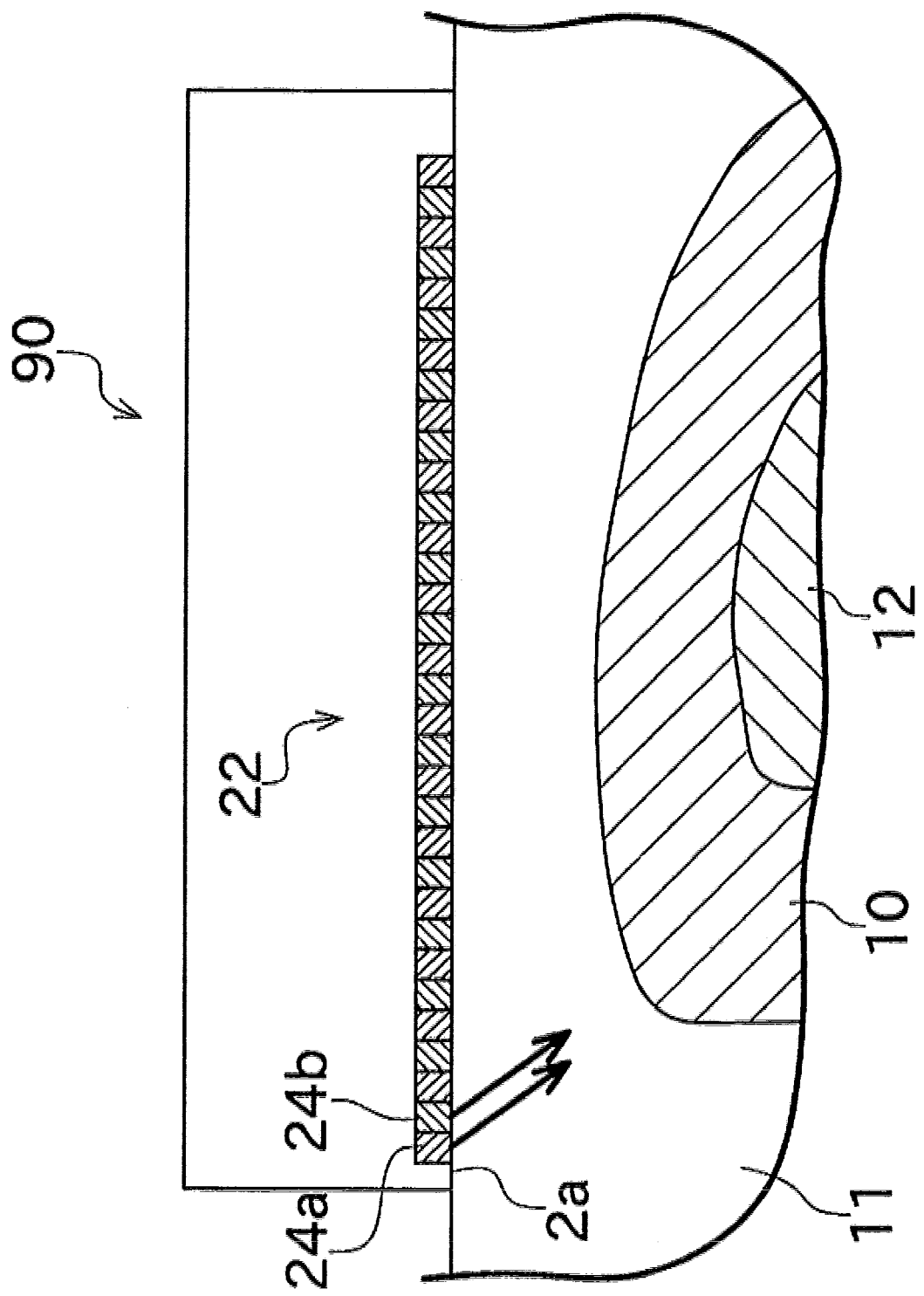
FIG. 15 is a schematic sectional view of an ultrasonic transceiver according to a modified example.

A configuration of an ultrasonic transceiver 90, according to the bone strength diagnostic apparatus 1, according to the modified example is shown in FIG. 15. The ultrasonic transceiver 90 includes only an array transducer 22 in which the plurality of transducers 24 are arranged at an equal interval in one line without the ultrasonic transmission dedicated transducer. Here, the array transducer 22 is provided so as to be extended to a position where the ultrasonic transmission dedicated transducer 21 is located in the above embodiment.

Here, the bone strength diagnostic apparatus 1 of the above embodiment may have the problems as below. Specifically, in the above embodiment, the shape in the vicinity of the incident point Pin of the ultrasonic wave on the cortical bone 10 cannot be detected when detecting the bone front surface line. This is because the shape detecting module 40, when detecting the front surface shape of the cortical bone, can detect only the shape immediately below the array transducer 22. Therefore, when calculating the propagation path of the surface propagation wave, the position of the incident point Pin is found based on the line presumed from the bone front surface line. However, in this method, the accurate position of the incident point Pin cannot be found, also leading to error of the speed-of-sound to be derived.

Consequently, the modified example eliminates the ultrasonic transmission dedicated transducer, and the transmission of the ultrasonic wave is performed also by the array transducer (linear array) 22 when measuring the speed-of-sound. For example, the transducer 24a and the transducer 24b are used in place of the ultrasonic transmission dedicated transducer 21 of the above embodiment.

Specifically, the adjacent transducer 24 transmits the ultrasonic wave at a timing shifted; therefore, the ultrasonic wave beam can be transmitted in the oblique direction. According to this, the array transducer 22 not only can function also as the ultrasonic transmission dedicated transducer 21 but also can transmit the ultrasonic wave at arbitrary angles. Thus, the ultrasonic wave can be radiated to the cortical bone 10 at a suitable angle (critical angle or angle near the critical angle). This can improve the efficiency and reduce the speed-of-sound error due to the directivity.

Furthermore, with the configuration as described above, the position of the incident point at which the ultrasonic wave enters the cortical bone 10 is always immediately below the array transducer 22, therefore, the position of the relevant incident point can be accurately calculated based on the result of detecting the bone front surface line by the shape detecting module 40. Additionally, since the ultrasonic transceiver 90 of the modified example has the array transducer 22 arranged across the full width thereof as shown in FIG. 15, the bone shape can be grasped entirely at the time of measurement, facilitating the measurement.

As described above, the ultrasonic transceiver included in the speed-of-sound measurement apparatus according to the modified example has the plurality of transducers 24 which are arranged at an equal interval in one line to constitute the array transducer 22, and at least one of which functions also as the ultrasonic transmission dedicated transducer 21 of the above embodiment.

This enables the transmission dedicated configuration to be eliminated, allowing the apparatus to be simplified. Further, the timing is shifted when the ultrasonic wave is transmitted from the adjacent transducer 24 and the time interval for shifting the timing is adjusted so the ultrasonic wave beam can be created at arbitrary angles. This enables the ultrasonic wave to be radiated to the front surface of the cortical bone 10 at an optimal angle. Moreover, in the case of the configuration where the plane wave is generated by the array transducer 22 to detect the front surface shape of the cortical bone 10, only the front surface shape at the position immediately below the array transducer 22 can be detected. Therefore, in the case of the configuration where the ultrasonic transmission dedicated transducer 21 and the array transducer 22 are arranged separately, the shape in the vicinity of the incident point on the front surface of the cortical bone cannot be detected. In this regard, since the transducer 24 functions as the ultrasonic transmission dedicated transducer 21, the shape in the vicinity of the incident point on the front surface of the cortical bone can be detected. This makes it possible to correctly calculate the propagation time.

Hereinbefore, the preferred embodiment and the modified examples thereof in the present invention are described; the above configuration may be modified as below, for example.

In the above embodiment, the description is given in which all the waveform signals outputted by the plurality of transducers 24 are integrated. However, all the waveform signals are not necessary to be integrated. For example, if the surface propagation wave is known not to come to a certain transducer 24, the waveform signal from the relevant transducer 24 does not have to be integrated.

Figure 16:
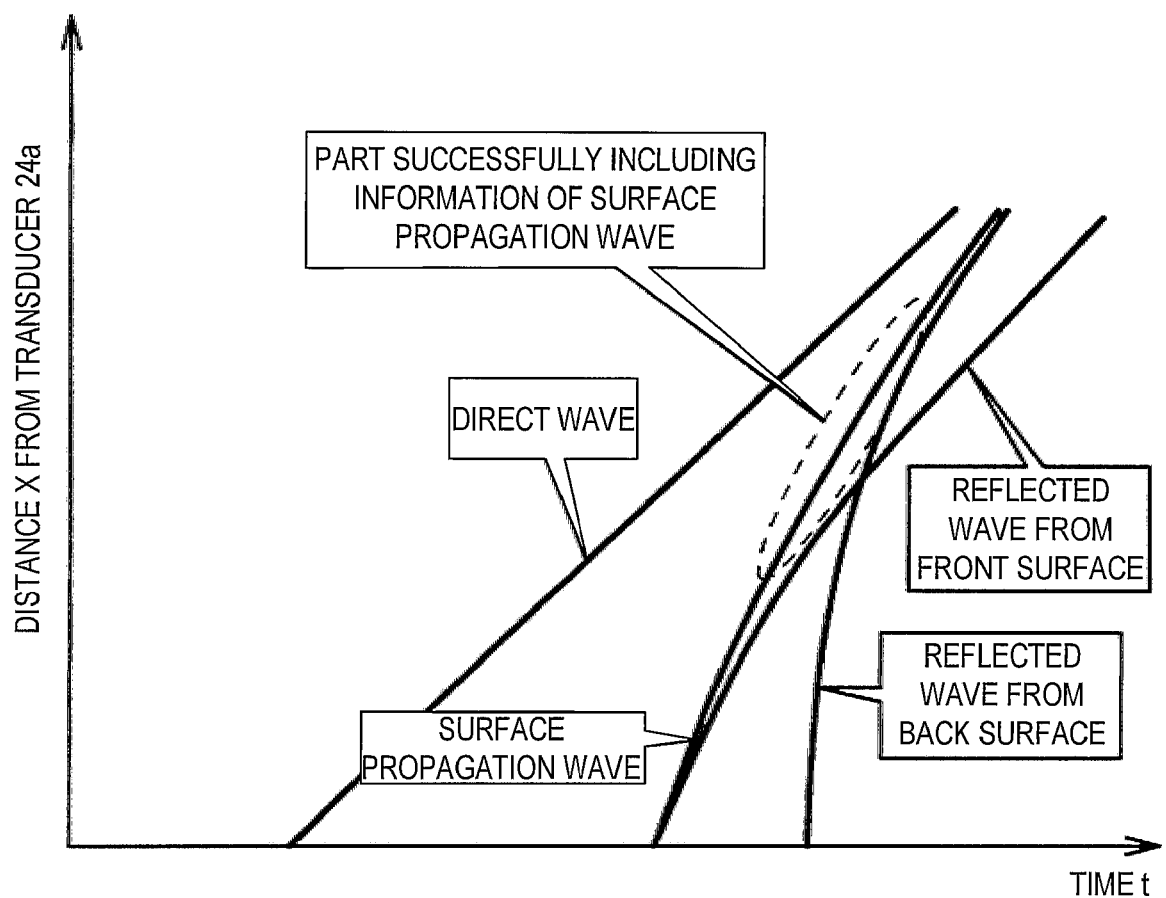
FIG. 16 is a graph showing a case where a reflected wave from the front surface and a reflected wave from the back surface are superimposed with respect to a surface propagation wave.

Further, there is a case where for example, the peaks of the direct wave, the reflected wave from the front surface, the reflected wave from the back surface and the surface propagation wave have the relationship as shown in FIG. 16. As shown in FIG. 16, after a certain point the surface propagation wave and the reflected wave from the front surface continuously separate from each other and the surface propagation wave arrives earlier. Whereas, the reflected wave from the back surface becomes closer to the surface propagation wave after a certain point and the wave is weighted. Therefore, the information of the surface propagation wave is most favorably included in a portion surrounded by a dotted line in the graph of FIG. 16 (in this portion, the peak of the surface propagation wave is not superimposed by the peaks of other waves). Consequently, in the case of integrating the waveform signals, only the waveform signals including the portion surrounded by the dotted line maybe selected to integrate, leading to the accurate measurement of the speed-of-sound.

Note that the point where the surface propagation wave and the reflected wave from the front surface separate from each other can be presumed from the front surface shape of the cortical bone, and can be used to select the waveform signals to integrate. On the other hand, a position where the surface propagation wave and the reflected wave from the back surface are superimposed is difficult to presume. However, even if all the waveform signals after the point where the surface propagation wave and the reflected wave from the front surface separate from each other are integrated (even if the waveform signal superimposed by the reflected wave from the back surface is integrated), the effects of the noise waveform can be suppressed according to the speed-of-sound measurement method of the invention, allowing the speed-of-sound to be suitably derived.

The above calculation module may be modified to be provided on the ultrasonic transceiver side. Further, the configuration is not limited to such a configuration where the ultrasonic transceiver and the apparatus main body are separated and the ultrasonic transceiver and the apparatus main body may be combined.

In the above embodiment, the presumed propagation time calculating module 51 is configured to find the propagation path and presumed propagation time of the refracted surface wave, but may also be configured to find the propagation path and presumed propagation time of the leaky surface wave. Even in this case, the waveform signals can be integrated to each other so the peak of the relevant leaky surface wave can be focused, allowing the speed-of-sound to be suitably measured.

The shape detecting module 40 may detect the shape of the back surface of the cortical bone 10 based on the back surface reflected wave when detecting the front surface shape of the cortical bone 10 based on the front surface reflected wave. In this case, a thickness of the cortical bone can be found based on the front surface shape and the back surface shape. The found thickness of the cortical bone can be used as one index of the health of the bone.

Further, the method for detecting the front surface shape of the subject's body by the shape detecting module 40 may be, in place of the method in which the waves are simultaneously transmitted from the plurality of transducers 24 to generated the plane wave, as follows, for example. That is, the ultrasonic wave is transmitted by one or the plurality of transducers 24 from the end of the array transducer 22 sequentially. Then, the front surface shape of the cortical bone 10 is found based on the period of time from when each transmission is performed to when the surface reflected wave is received.

According to the above shape detection method, the measurement takes some time because the ultrasonic wave sequentially is transmitted from each of the plurality of transducers 24. However, even if the front surface of the subject's body is concave, the front surface shape can be correctly detected. On the other hand, as described in this embodiment, in the method in which the waves are simultaneously transmitted from the plurality of transducers 24 to generate the plane wave, despite the measurement time being reduced, the front surface shape cannot be measured in the case of the concave front surface of the subject's body. A shape of the tibia section varies and may include a concave part in a portion. Therefore, the bone strength diagnostic apparatus 1 of the above embodiment may not be able to accurately find the front surface shape of the cortical bone 10.

Consequently, if an error occurs in the case of measuring the front surface shape of the cortical bone 10 by the method as described in above embodiment where the plane wave is generated (if the section shape of the cortical bone 10 includes the concave part), the above method may be especially preferable in being used in which the ultrasonic wave is transmitted by the transducer 24 from the end of the array transducer 22 sequentially.

In the above embodiment, the waveform integrating module 52 is configured to find the amplitude of the envelope of the integrated waveform as the validity index value, but is not limited thereto. For example, with a configuration where the amplitude itself of the integrated waveform is used as the validity index value also can detect whether or not the peaks of the waveform signals are strengthened to each other (i.e., whether or not the speed-of-sound presumed value is correct). Moreover, for example, there may be a configuration where an integration value (area) of the integrated waveform is used as the validity index value.

Further, the above embodiment and the modified examples are configured to shift the waveform signal and thereafter find the integrated waveform or the multiplied waveform, and then determine the validity of the presumed propagation time, but not limited to this configuration. Specifically, the waveform signal outputted by each transducer 24, without being shifted, can be directly compared with the presumed propagation time curve (t-x curve) to determine the speed-of-sound. In this case, the waveform signal may be used as it is, and may be subjected to the process in which the amplitude is extracted.

For example, data of the waveform signal as shown in FIG. 3 is taken as a two-dimensional image and compared with the t-x curve as shown in FIG. 8 to find the index (validity index value) indicating a degree of coincidence. As the method for directly comparing the waveform signal and the t-x curve described above, a feature extraction method (e.g., generalized Hough transform), which is used for a digital image processing of related art, and a pattern recognition technique (using the neural network and the like) may be used. Then, the degrees of coincidence of the various t-x curves as shown in FIG. 12 are obtained with the speed-of-sound presumed value being varied, and the speed-of-sound presumed value of the t-x curve having the highest degree of coincidence is employed as the measurement value of the speed-of-sound.

Using the above method also, the speed-of-sound can be stably measured with the effects of the noise suppressed, similarly to the method in which the waveform signal is shifted to be integrated or multiplied. That is, even if the respective waveform signals include the noises, the waveform signals from the plurality of transducers 24 can be used to perform the above feature extraction, the pattern recognition and the like. Thus, the effects of the noises are reduced and the validity index value can be favorably found. The configuration is configured to take the degree of coincidence between the waveform signal and the t-x curve into consideration; therefore, there can be determined whether or not the presumed propagation time is valid without the peak position being strictly found from the waveform signal.

The speed-of-sound in the soft tissue may be changed depending on the thickness of the soft tissue. Note that generally the thicker the soft tissue, the more the fat is included in the soft tissue; thus, the thicker the soft tissue, the slower the speed-of-sound in the relevant soft tissue.

In the above embodiment, the waveform signal outputted by each transducer 24 is multiplied by the window function, but calculation using the window function may be eliminated.

Further, the shape detecting step may be eliminated, and the presumed propagation time may be calculated with the assumption, for example, the section contour shape of the cortical bone 10 is linear. However, in the case of the measurement of the speed-of-sound in the circumferential direction of the bone, since the section contour of the front surface of the cortical bone 10 is curved, the error becomes large with the above assumption of the propagation path. Therefore, it is preferable to detect the front surface shape of the cortical bone and calculate the presumed propagation time based on the front surface shape.

Figure 17:
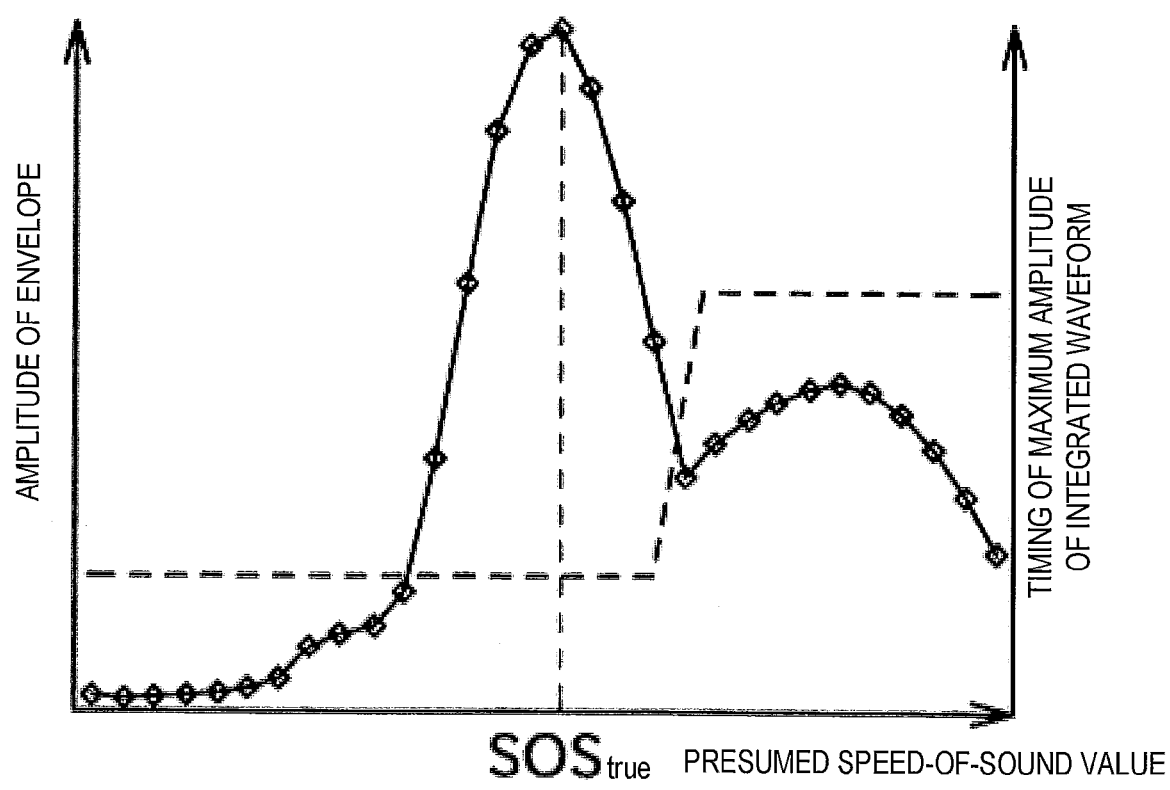
FIG. 17 is a graph in which the time when the integrated waveform has a maximum amplitude and is additionally plotted in the graph of FIG. 13.

There is a case where the speed-of-sound presumed value having the maximum amplitude of the envelope of the integrated waveform is generated in plural numbers as shown in the graph of FIG. 13. In this case, a time when the amplitude of the integrated waveform has the maximum value may be subsidiary used as information for making a decision which speed-of-sound presumed value to employ as the measurement value. FIG. 17 is a graph in which a time when the integrated waveform has the maximum amplitude is additionally plotted in the graph of FIG. 13. If there are two speed-of-sound presumed values having the maximum amplitude of the envelope of the integrated waveform (as is in the case of the graph of FIG. 17), it can be considered one is the case where the peaks of the surface propagation waves are strengthened to each other to enlarge the amplitude of the envelope, and the other is the case where, for example, the peaks of the reflected wave from the back surface are strengthened to each other to enlarge the amplitude of the envelope. As shown in FIG. 17, if the time of the maximum amplitude of the integrated waveform (i.e., the time when the peaks strengthen to each other are detected) is plotted, it is easy to confirm the peak strengthened is changed. This can be used as an index representing whether or not the surface propagation wave is focused on.

Further, the speed-of-sound measurement method and speed-of-sound measurement apparatus of the present invention can be widely used for applications to measure the speed-of-sound of other than the bone. Especially, the speed-of-sound measurement method and the speed-of-sound measurement apparatus of the present invention are significantly effective when the speed-of-sound of the subject's body having the non-linear front surface shape is measured under an environment with many noises.

In the foregoing specification, specific embodiments of the present invention have been described. However, one of ordinary skill in the art appreciates that various modifications and changes can be made without departing from the scope of the present invention as set forth in the claims below. Accordingly, this specification and figures are to be regarded in an illustrative sense rather than a restrictive sense, and all such modifications are intended to be included within the scope of the present invention. The benefits, advantages, solutions to problems, and any element(s) that may cause any benefit, advantage, or solution to occur or become more pronounced are not to be construed as critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "approximately" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

What is claimed is:

1. A speed-of-sound measurement apparatus, comprising:
a wave transmission module for transmitting an ultrasonic wave to a front surface of a subject's body;
a plurality of wave reception modules which each receives the ultrasonic wave from the subject's body and outputs a waveform signal corresponding to the received ultrasonic wave;
a presumed propagation time calculating module for calculating a propagation time from when the ultrasonic wave is transmitted by the wave transmission module to when the ultrasonic wave arrives at each of the wave reception modules after propagating along the front surface of the subject's body or inside the subject's body, based on a presumed value of speed-of-sound in the subject's body and a front surface shape of the subject's body;
a validity index value calculating module for finding a validity index value to be an index of validity of the propagation time based on the waveform signals outputted by at least two of the plurality of wave reception modules; and
a speed-of-sound deriving module for finding the speed-of-sound in the subject's body based on the validity index value.

2. The speed-of-sound measurement apparatus of claim 1, wherein the validity index value calculating module shifts respectively the waveform signals outputted by the at least two of the plurality of wave reception modules by a time corresponding to the propagation time, finds an integrated waveform obtained by integrating the shifted waveform signals to each other, and finds the validity index value based on the integrated waveform.

3. The speed-of-sound measurement apparatus of claim 2, wherein the presumed propagation time calculating module calculates the propagation time based on a shape of the front surface of the subject's body measured in advance.

4. The speed-of-sound measurement apparatus of claim 1, wherein the validity index value calculating module shifts respectively the waveform signals outputted by the at least two of the plurality of wave reception modules by a time corresponding to the propagation time, finds a multiplied waveform obtained by multiplying the shifted waveform signals with each other, and finds the validity index value based on the multiplied waveform.

5. The speed-of-sound measurement apparatus of claim 4, wherein the presumed propagation time calculating module calculates the propagation time based on a shape of the front surface of the subject's body measured in advance.

6. The speed-of-sound measurement apparatus of any one of claims 1 to 4, wherein the presumed propagation time calculating module calculates the propagation time using plural kinds of values as the presumed value of speed-of-sound;
the validity index value calculating module finds, in response to the plural kinds of presumed values of speed-of-sound, the validity index value for each kind; and
the speed-of-sound deriving module finds the speed-of-sound in the subject's body based on the validity index value for each of the plural kinds of presumed values of speed-of-sound.

7. The speed-of-sound measurement apparatus of claim 6, wherein the presumed propagation time calculating module calculates the propagation time based on a shape of the front surface of the subject's body measured in advance.

8. The speed-of-sound measurement apparatus of claim 1, wherein the presumed propagation time calculating module calculates the propagation time based on a shape of the front surface of the subject's body measured in advance.

9. The speed-of-sound measurement apparatus of claim 1, further comprising a shape detecting module;
wherein at least a part of the plurality of wave reception modules is configured to transmit the ultrasonic wave to the front surface of the subject's body;
the shape detecting module detects the shape of the front surface of the subject's body based on a period of time from when the ultrasonic wave is transmitted to when the ultrasonic wave arrives at each of the wave reception modules after reflected on the front surface of the subject's body; and
the presumed propagation time calculating module calculates the propagation time based on the shape of the front surface of the subject's body detected by the shape detecting module.

10. The speed-of-sound measurement apparatus of claim 1, wherein the plurality of wave reception modules constitutes a linear array in which the wave reception modules are arranged at an equal interval in one line, and at least any one of the plurality of wave reception modules functions as the wave transmission module.

11. A method for measuring speed-of-sound using a speed-of-sound measurement apparatus including a plurality of wave reception modules which each outputs a waveform signal in response to an ultrasonic wave received, the method comprising:
transmitting an ultrasonic wave to a front surface of a subject's body;
receiving the ultrasonic wave from the subject's body by each of the plurality of wave reception modules;
calculating a propagation time from when the ultrasonic wave is transmitted to when the ultrasonic wave arrives at each of the wave reception modules after propagating along the front surface of the subject's body or inside the subject's body, based on a presumed value of speed-of-sound in the subject's body and a shape of the front surface of the subject's body; and
finding a validity index value to be an index of validity of the propagation time based on the waveform signals outputted by at least two of the plurality of wave reception modules;
wherein the calculating the propagation time and the finding the validity index value are repeated with the presumed value of speed-of-sound being varied so that a validity index value is found for each of plural kinds of presumed values of speed-of-sound and the speed-of-sound in the subject's body is found based on the validity index value for the each kind.

12. The method for measuring speed-of-sound of claim 11, wherein the finding the validity index value includes shifting the waveform signals outputted by the at least two of the plurality of wave reception modules respectively by a time corresponding to the propagation time, integrating the shifted waveform signals to each other to find an integrated waveform, and finding the validity index value based on the integrated waveform.

13. The method for measuring speed-of-sound of claim 11, wherein the finding the validity index value includes shifting the waveform signals outputted by the at least two of the plurality of wave reception modules respectively by a time corresponding to the propagation time, multiplying the shifted waveform signals by each other to find a multiplied waveform, and finding the validity index value based on the multiplied waveform.

14. The method for measuring speed-of-sound of any one of claims 11 to 13, further comprising detecting the shape of the front surface of the subject's body;
wherein the calculating the propagation time includes calculating the propagation time based on the shape of the front surface.

\* \* \* \* \*